United States Patent
Kitano et al.

Patent Number: 5,840,016
Date of Patent: Nov. 24, 1998

[54] LINE CHANGEOVER DEVICE FOR ENDOSCOPE

[75] Inventors: Seiji Kitano, Hachioji; Hideo Ito, Akishima; Tsutomu Ishiguro, Hachioji; Yoshiyuki Tanii, Hamura; Satoshi Nakagawasai, Tokyo; Yasuhito Kura, Hino, all of Japan

[73] Assignee: Olympus Optical Co., Ltd., Tokyo, Japan

[21] Appl. No.: 659,932

[22] Filed: Jun. 7, 1996

[30] Foreign Application Priority Data

Oct. 24, 1995 [JP] Japan ................................ 7-275948

[51] Int. Cl.⁶ .................................................... A61B 1/12
[52] U.S. Cl. ................................... 600/159; 251/335.2
[58] Field of Search ........................... 600/153, 154, 600/155, 156, 157, 158, 159; 251/335.2

[56] References Cited

U.S. PATENT DOCUMENTS

| 4,694,821 | 9/1987 | Kondo . | |
| 4,694,848 | 9/1987 | Jorgensen et al. | 251/355.2 X |
| 5,027,791 | 7/1991 | Takahashi . | |

FOREIGN PATENT DOCUMENTS

| 69913 | 1/1983 | European Pat. Off. ............... 600/159 |
| HEI 2-54087 | 11/1990 | Japan . |
| HEI 3-15049 | 4/1991 | Japan . |
| 7-067831 A | 3/1995 | Japan . |
| 7-079910 A | 3/1995 | Japan . |
| 7-275189 A | 10/1995 | Japan . |

*Primary Examiner*—Beverly M. Flanagan
*Attorney, Agent, or Firm*—Armstrong, Westerman, Hattori, McLeland & Naughton

[57] ABSTRACT

A line changeover device for an endoscope, which changes over a line which is arranged in the endoscope, is arranged such that it comprises a cylinder and a piston which is fitted and inserted into the cylinder in a retractable manner, a seal member which is abutted against the cylinder for retaining at least one of water tightness and gas tightness with respect to the cylinder is fixedly provided on an outer periphery of the piston, and a strength reinforcement is provided on at least a part between an outer periphery of said seal member and an inner periphery thereof. The water tightness and the gas tightness within the cylinder are retained or held, and a sliding resistance of the piston is kept appropriately or adequately without the use of lubricating oil. Sliding ability between the cylinder and the piston at the time of operation is improved. Operability can be made fine or satisfactory.

18 Claims, 25 Drawing Sheets

UPPER SURFACE

LOWER SURFACE a < b

F1 < F2 a > b

F1 > F2

UPPER SURFACE

LOWER SURFACE

LINE CHANGEOVER DEVICE FOR ENDOSCOPE

BACKGROUND OF THE INVENTION

1. Field of the Invention

The invention relates to a line changeover device for an endoscope, which executes or performs line changeover in a fluid line (such as, a gas-feeding and water-feeding line or the like) which is provided in the endoscope.

2. Discussions of Relevant Art

An endoscope is arranged such that an illumination window and an observation window are provided at a tip or a forward end of an insertion thereof, so as to be able to observe the interior of a body cavity through the observation window.

More particularly, since, in a medical endoscope, the observation window is contaminated or polluted by body liquid or the like, a gas-feeding and water-feeding nozzle is provided which performs gas feeding and liquid feeding toward the observation window, in order to perform cleaning of the observation window and to supply air into the body cavity to swell out or bulge the body cavity to thereby secure observation visual field. This structural arrangement is such that cleaning water, pressurized air or the like is supplied to this gas-feeding and water-feeding nozzle through a fluid line. Thus, air or the cleaning liquid can be jetted from a forward end of the insertion.

Generally, in an endoscope which is provided with the fluid line, a gas-feeding tube and a water-feeding tube, which are made of a flexible or resilient tube, are inserted in and pass through the interior of the insertion of the endoscope; and a line changeover device which is made of a valve or the like, which is in communication with these tubes to perform line changeover, is provided in the vicinity of an operation. The structural arrangement is such that the line changeover device is operated whereby operation changeover or the like between the gas feeding and the water feeding can be performed.

In such a line changeover device for the endoscope, as disclosed in, for example, U.S. Pat. No. 4,694,821 and U.S. Pat. No. 5,027,791, there is a line changeover device which is arranged by a valve which has a cylinder and a piston. In this prior-art line changeover device, seal members are provided around the piston which slides within the cylinder, to keep water tightness and gas tightness of a passage between the piston and the cylinder. If wall thickness of each of the seal members is reduced, the seal members are deformed with respect to movement or motion of the piston in a movable direction. Thus, there is a fear that the water tightness and the gas tightness cannot be kept. For this reason, in order that the water tightness and the gas tightness are not lost by the movement of the piston, the wall thickness of each of the seal member in the movable direction is thick over the entire periphery such that durability is caused to be had in strength with respect to the movement in the movable direction.

Like the aforesaid prior-art line changeover device, if the wall thickness of each of the seal members increases, a sliding resistance of the piston increases. In view of this, in order that the piston is smoothly slidable, such a countermeasure is taken that lubricating oil (such as silicon oil or the like) is applied to the seal members so that the seal members can be moved smoothly.

Further, Japanese Patent Publication No. HEI 2-54087 (54087/1990) discloses a structural arrangement, which is provided with a suction changeover valve, for performing push operation of an operation button to cause suction operation to be performed, and a gas-feeding and water-feeding changeover valve for performing push operation of the operation button and such operation that a leak bore or hole which is provided in the operation button is closed by a finger to perform the water-feeding operation and the gas-feeding operation.

Similarly to the devices in the aforesaid U.S. Pat. No. 4,694,821 and U.S. Pat. No. 5,027,791, this gas-feeding and water-feeding changeover valve is so arranged as to comprise a piston to which the operation button is connected, and a cylinder into which this piston is fitted. Seal members are provided for keeping water tightness and gas tightness of a passage with respect to the cylinder, around the piston which slides within the cylinder.

In the device disclosed in Japanese Patent Publication No. HEI 2-54087, notice is made to the operation ability or the operation capacity of a spring, and the push-operation start capacity from waiting time of the operation button in the suction changeover valve and the gas-feeding and water-feeding changeover valve is set larger in the gas-feeding and water-feeding changeover valve than the suction changeover valve, to improve operability of the operation button for gas feeding and water feeding.

As previously described, in the prior-art line changeover device for the endoscope, the following is performed. Specifically, the seal members which are provided around the piston which slides within the cylinder are such that, in order to cause each of the seal members to have durability in strength with respect to the movement of the piston in the movable direction to hold or retain the water tightness and the gas tightness, the wall thickness in the movable direction is formed thick over the entire periphery thereof. Furthermore, lubricating oil (such as, silicon oil or the like) is applied to the seal members in such a manner that the piston can slide smoothly.

However, there are the following problems or the like. Specifically, in a case where the lubricating oil (such as, the silicon oil or the like) is applied, variation is produced in the sliding resistance by an amount of application. However, with such a structural arrangement, a significant amount of labor is needed by wiping operation because it is necessary to wipe out all the lubricating oil when the piston is cleaned, and the like.

On one hand, in a case where the lubricating oil is not applied in order to avoid this deficiency, the following problem occurs. Specifically, since, in the prior-art structural arrangement, the wall thickness of each of the seal members in the movable direction increases in view of the reason on the strength, the sliding resistance of the piston increases, and the operability becomes deteriorated.

Further, in the prior-art line changeover device for the endoscope, consideration is paid only to the push capacity at the time of push operation, and the arrangement is such that only an operation force of the operation button is improved. No consideration has particularly been paid to slidability between the seal members which are provided on the piston, and the cylinder at the time the piston of the operation button for gas feeding and water feeding slides within the cylinder. For this reason, when the piston slides within the cylinder by operation of the operation button, deformation occurs in the seal members by friction with respect to the cylinder. At this time, however, there was a fear that an outer periphery of each of the seal member excessively receives urging deformation, and sliding characteristics of the piston are deteriorated.

Moreover, the prior-art arrangement has had the following fear. Specifically, the outer periphery of each of the seal members excessively receives the urging deformation. Consequently, the frictional force between the seal members and the cylinder increases, and the operation capacity of the piston increases so that slidability of the piston is deteriorated.

In order to solve this problem, an amount of deformation of a seal of each of the seal members at an outer periphery should be reduced to reduce the frictional force between the seal members and the cylinder. In this case, however, there is a fear that the strength of the seal becomes insufficient so that the water tightness and the gas tightness that are original functions of the seal members cannot be kept. In order to secure the strength of the seal, it is necessary to increase the seal. In this case, however, there is a problem that the frictional force between the seal members and the cylinder increases, as described previously, so that slidability of the piston is deteriorated.

OBJECTS AND SUMMARY OF THE INVENTION

An object of the present invention is to provide a line changeover device for an endoscope, which can keep strength, in a movable direction, for each of the seal members which are provided around a piston in order to prevent deformation of a piston by sliding resistance to thereby hold or retain water tightness and/or gas tightness within a cylinder, and can suitably keep or maintain a sliding resistance of the piston without the use of lubricating oil in order to improve slidability between the cylinder and the piston at the time of operation, and is superior in operability and is also easy in terms of handling at the time of cleaning.

It is another object of the present invention to provide a line changeover device for an endoscope, which can reduce the capacity required for sliding movement of a piston, improves operability, and can reduce labor or trouble for a user.

It is the other object of the present invention is to provide a line changeover device for an endoscope, in which there is smaller or less in such deformation that the whole of each of seal members is heaved or the like, and an excessive sliding resistance of the seal members can be eliminated, so that slidability of a piston is improved.

According to the invention, there is provided a line changeover device for an endoscope, which is so arranged as to comprise a cylinder, and a piston which is fitted and inserted into the cylinder in a retractable manner, for changing over a line which is arranged in the endoscope, wherein seal members each of which is abutted against said cylinder to retain at least one of water tightness and gas tightness with respect to the cylinder is fixedly provided on an outer periphery of said piston, and a strength reinforcement is provided on at least a part between an outer periphery and an inner periphery of each of said seal members.

Other features and advantages of the present invention will sufficiently become apparent from the following explanation.

BRIEF DESCRIPTION OF THE DRAWINGS

FIGS. 1 to 10 relate to a first enforcement form of the invention;

FIG. 1 is an arrangement explanatory view showing the whole arrangement of an endoscope apparatus;

FIG. 2 is a cross-sectional view showing an arrangement of a gas-feeding and water-feeding valve which serves as a line changeover device;

FIG. 3 is a perspective view showing an arrangement of seal members in the first enforcement form;

FIG. 5 is a cross-sectional view showing a form or configuration of each of the seal members under a natural state;

FIG. 6 is a cross-sectional view showing a deformed state of each of the seal members at the time of sliding within a cylinder;

FIG. 9 is a cross-sectional view showing a form of the valve body under a natural state;

FIG. 10 is a cross-sectional view showing a deformed state of the valve body at the time of sliding within the cylinder;

FIGS. 18 to 25 relate to a second enforcement form of the present invention;

FIG. 18 is a cross-sectional view showing a first arrangement example of the strength reinforcement which is provided on the seal members;

FIG. 20 is a side elevational view showing a modification of the first arrangement example of the strength reinforcement;

FIG. 21 is a side elevational view showing another modification of the first arrangement example of the strength reinforcement;

FIG. 22 is a cross-sectional view showing a second arrangement example of the strength reinforcement which is provided on the seal members;

FIG. 24 is a side elevational view showing a modification of the second arrangement example of the strength reinforcement;

FIG. 25 is a side elevational view showing another modification of the second arrangement example of the strength reinforcement;

FIG. 26A is a top plan view in which the seal members in the third enforcement form are viewed from the side of an upper surface thereof;

FIG. 26B is a top plan view in which the seal members in the third enforcement form are viewed from the side of a lower surface thereof;

FIG. 27 is an explanatory view in which the seal members in the third enforcement form are developed;

FIG. 28 is an explanatory view in which the seal members in the first enforcement form are developed;

DETAILED DESCRIPTION OF THE PREFERRED EMBODIMENTS

Figure 1:
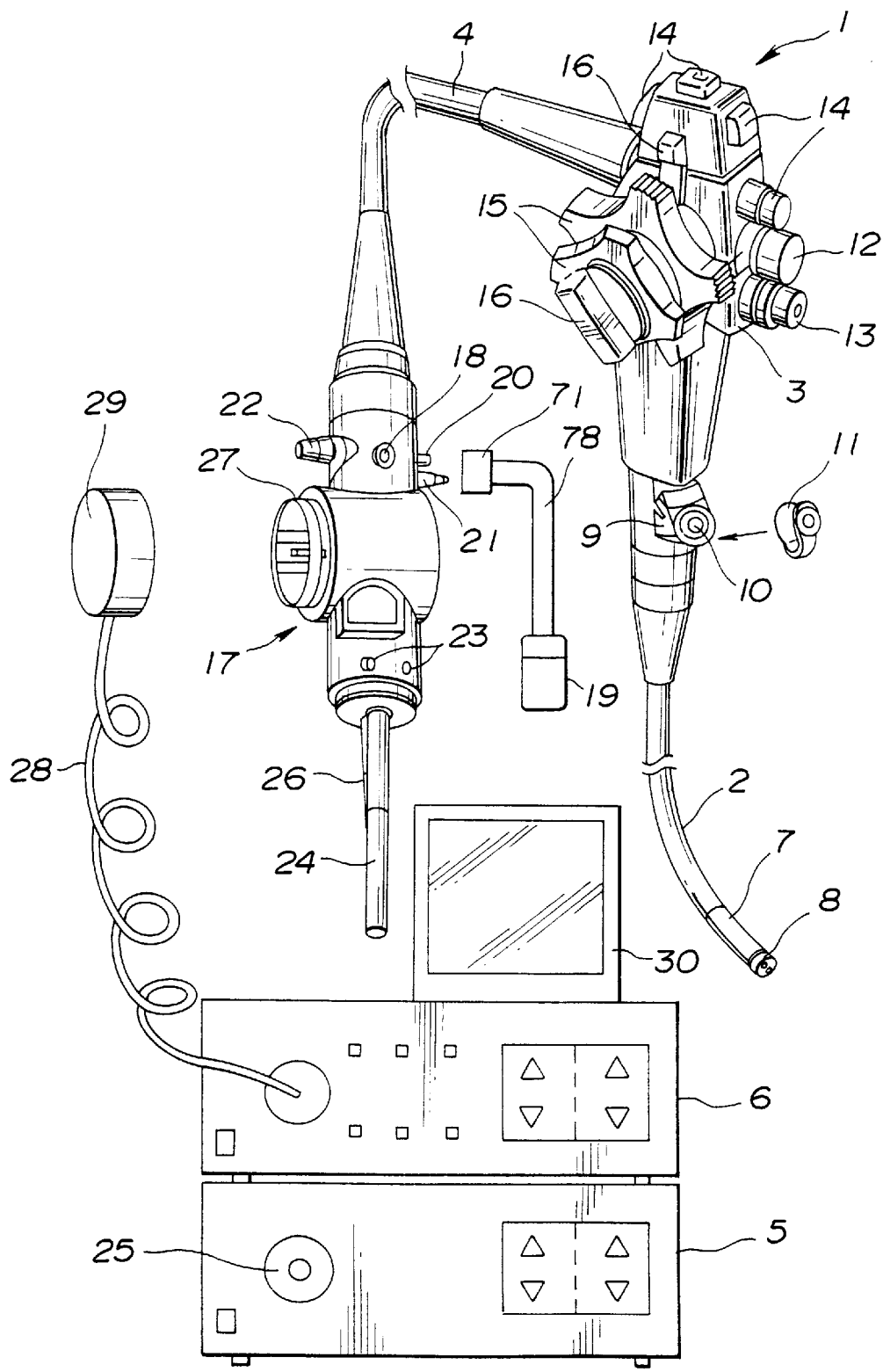
Figure 10:
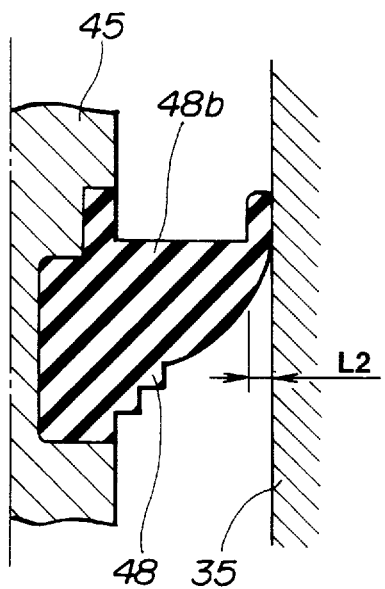

A first enforcement form of the present invention is shown in FIGS. 1, to 10.

As shown in FIG. 1, an endoscope 1 which is provided in an endoscope apparatus, is so arranged as to have an elongated insertion 2, an operation 3 which is gripped by a user to perform operation, and a connection code 4 for being connected to a light source device 5 and a video processor 6. The insertion 2 is covered by resin (such as, polyurethane or the like), and is provided, at a forward-end portion thereof, with a curve-able or bendable curvature 7 which is covered with a soft elastic body.

A forward-end hard quality 8 is provided at a forward end of the curvature 7. An observation optical system, an image pick-up element, an illumination optical system, a gas-feeding and water-feeding nozzle and the like are provided on this forward-end hard quality 8. Further, the forward-end hard quality 8 is provided with one of openings for a forceps channel which extends in the interior of the insertion 2. On one hand, the other opening of the forceps channel is provided in a forceps port cover 9 of the operation 3, as a forceps opening 10. The arrangement is such that a forceps plug 11 is mounted to this forceps opening 10, as occasion demands.

The operation 3 is provided with a suction-line changeover device 12 which is operated when suction is performed, a gas-feeding and water-feeding line changeover device (called also as a gas-feeding and water-feeding valve) 13 which is operated when gas feeding and water feeding are performed, and remote switches 14 for performing various kinds of treatments or processings of a video signal which is obtained by the image pickup element at the forward end thereof. Moreover, angle knobs 15 made of hard resin are provided at the operation 3. The arrangement is such that these are operated whereby the curvature 7 can be curved in upward and downward, and left and right directions. Furthermore, an engagement lever 16 made of hard resin, which is used when the curvature 7 is kept under a curved fixing state and when the curved fixing state is released, is provided on the upper part of the angle knobs 15.

The connection code 4 is covered by resin (such as polyurethane or the like), and a connector 17 which is formed by hard resin is mounted to a forward end thereof. The connector 17 is provided with an earth terminal 18 on a side periphery on the side of a code, for returning high-frequency leakage current to a power source of a cauterization device, a pressurization pipe 20 and a water-feeding pipe 21 made of a metal, for being connected to a water-feeding tank 19 to perform water feeding, and a suction base 22 for being connected to an unshown suction pump to perform suction, and is provided, on the side of the forward end thereof, with electric contacts 23, and a light guide end 24. The arrangement is such that the connector 17 is connected to a connector receptor 25 of the light source device 5, whereby illumination light from the light source device 5 is transmitted to the light guide which extends in the interior of the endoscope, so as to be outputted from the illumination optical system of the forward-end hard quality 8.

Moreover, a gas-feeding pipe 26 is provided in projection on the side of the forward end of the connector 17 substantially in parallel with the light-guide end 24. The arrangement is such that pressurized air from the pump within the light source device 5 is sent or fed to the gas-feeding pipe 26.

Furthermore, an electric connector 27 is provided on a side surface of the connector 17. The structural arrangement is such that a connector receptor 29 of a connection code 28 which extends from the video processor 6 is connected to this electric connector 27 so as to be connected to the video processor 6, whereby an electric signal which is outputted from the image pick-up element at the forward end of the endoscope is processed in signal by the video processor 6 so that the electric signal can be projected onto a monitor 30 as an endoscope image.

Subsequently, a detailed arrangement of the gas-feeding and water-feeding valve 13 which serves as the gas-feeding and water-feeding line changeover device will be described on the basis of FIG. 2.

The gas-feeding and water-feeding valve 13 comprises a cylinder 31 and a piston 32. In FIG. 2, the left side shows a natural state of the piston 32, while the right side shows a pressed or forced state of the piston 32.

A mounting hole 34 is provided in boring in a casing 33 which forms the operation 3. The cylinder 31 is fixed to this mounting hole 34 by means to be described later. The piston 32 is detachably fitted and inserted with respect to this cylinder 31.

The cylinder 31 is so formed as to comprise a substantially cylindrical stepped cylinder body 35 made of a metal. In order from the opening side toward the bottom side, a gas-feeding line 36 that is a gas outlet which is in communication with a gas-feeding and water-feeding nozzle 221 (refer to FIG. 32) at the forward end of the endoscope, a gas-feeding line 37 that is a gas inlet which is in communication with the connector 17 at the end of said connector code 4, a water-feeding line 38 that is a liquid outlet which is in communication with said gas-feeding and water-feeding nozzle 221, and a water-feeding line 39 that is a liquid inlet which is in communication with said water-feeding tank 19 and the water-feeding pipe 21 are provided in the side wall of the cylinder body 35.

Threads 40 are formed in an end of the opening in said cylinder body 35. A base 41 is screwed into the threads 40 from the outside of the casing 33 of the operation 3, whereby the cylinder body 35 is fixed to the casing 33 in such a form that the casing 33 is put from both inside and outside. The base 41 has an outer periphery thereof which is provided therein with a jig hole 42 into which a jig for rotating the base 41 can be inserted.

The base 41 has an upper flange 41a and a lower flange 41b. An O-ring 44 within an annular groove 43, which is formed in an inner peripheral surface of the mounting hole 34, is compressed by the lower flange 41b to seal the mounting hole 34, whereby gas and liquid are prevented from invading into the interior of the operation 3.

The piston 32 is so arranged as to have a substantially cylindrical piston body 45 made of a material which has rigidity (such as a metal, synthetic resin or the like). This piston body 45 is provided, in the interior thereof, with a communication path 46 in the direction of a longitudinal axis thereof. An opening 47 which opens in a side direction is formed in a lower-end of the communication path 46.

A valve body 48 made of an elastic material is insert-formed in the piston body 45 at an upper part of said opening 47. A coming-out prevention tube or cylinder 49 and a presser member 50 are threadedly engaged with an upper part of the piston body 45. A seal support member 51 is clamped between the coming-out prevention cylinder 49 and the piston body 45. A seal member 53 is insert-formed in a side of the seal supporting member 51 in the orbital form, and a slider 52 is provided at a lower-end thereof.

The seal member 53 of the seal supporting member 51 is so arranged as to have strength reinforcements 53b between an outer periphery of the seal member 53 and an inner periphery thereof every predetermined intervals. Further, a seal 53a which is in contact with the inner surface of the cylinder body 35 so as to be deformed when said piston body 45 is fitted and inserted into said cylinder body 35 is provided on an outer peripheral end of the seal member 53.

In order to reduce a sliding resistance at the time the seal member 53 slides within the cylinder body 35, it is necessary that the seal member 53 is apt to be deformed when the seal 53a of the seal member 53 is in contact with the inner surface of the cylinder body 35 so as to be deformed. Specifically, the wall thickness of a contact (seal 53a) with respect to the cylinder body 35 of the seal member 53 should be reduced. However, in a case where the wall thickness is reduced, the piston 32 of the gas-feeding and water-feeding valve 13 is moved in a vertical direction in FIG. 2. Therefore, the seal member 53 is deformed. Thus, the water tightness and the gas tightness cannot be kept. There is a fear that function of the gas-feeding and water-feeding valve 13 is not performed. In view of this, by the fact that the strength reinforcements 53b are provided on parts of the seal member 53 as is in the present enforcement form, it is possible to prevent the seal member 53 from being excessively deformed with respect to the sliding movement of the piston 32. It is possible to prevent the water and air from leaking due to the excessive deformation.

Figure 3:
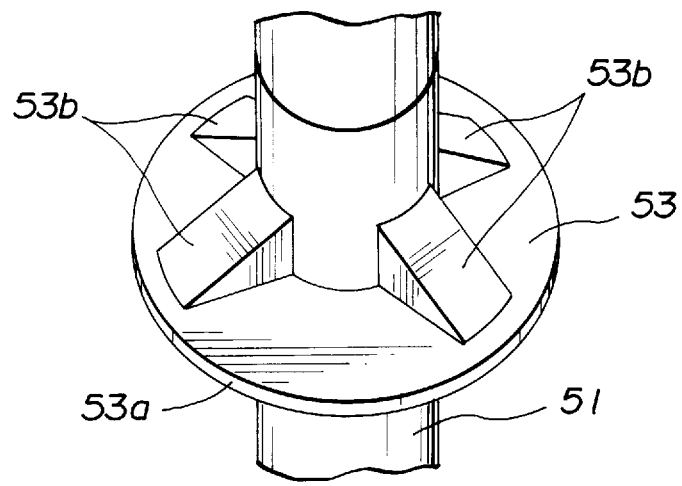
Figure 4A:
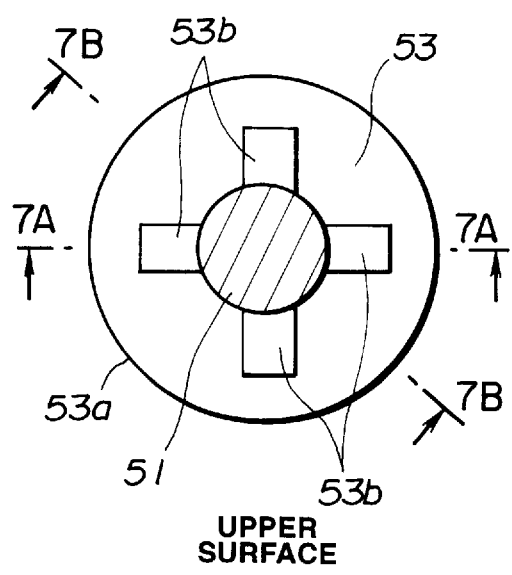
FIG. 4A is a top plan view in which the seal members in the first enforcement form are viewed from the side of an upper surface thereof.
Figure 4B:
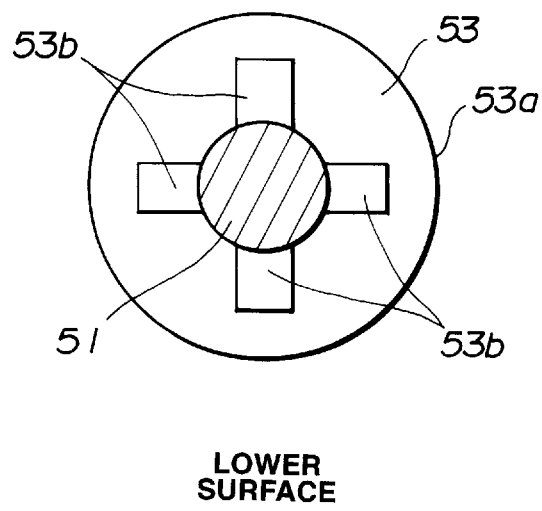
FIG. 4B is a top plan view in which the seal members in the first enforcement form are viewed from the side of a lower surface thereof.

The strength reinforcements 53b are provided respectively on upper and lower surfaces of the seal member 53 (i.e., in four on the upper surface thereof and in four on the lower surface thereof, as shown in, e.g., FIG. 3 and FIGS. 4A and 4B) if a surface close to a finger application 63 is assumed to be the upper surface, and the opposite surface is assumed to be the lower surface in the seal member. The strength reinforcements 53b which are provided four on each of these upper and lower surfaces are provided at positions symmetrical in vertical direction to each other so as to take the same position, at least, at portions which are not ranges or regions adjacent to each other, of the fact that the outer periphery of the circular seal member 53 is divided in equal intervals, and at the upper and lower surfaces of the seal member 53 as shown in FIGS. 4A and 4B.

In this manner, the strength reinforcements which partially increase in wall thickness are provided in the seal member so as to cause the resistance force to be had with respect to the deformation of the seal member due to the sliding resistance of the piston, while the wall thickness of the outer periphery of the seal member is thinned to prevent the sliding resistance in the piston from becoming excessive, whereby it is possible to improve operability while keeping the water tightness and the gas tightness.

Further, a presser member 54 is threadedly engaged with the lower end of the piston body 45, and a seal supporting member 55 is clamped between the presser member 54 and the piston body 45. A seal member 56 is insert-formed in a side of this presser member 54 in an orbital manner. Moreover, a seal member 58 is also insert-formed similarly in a side of the seal supporting member 55 in an orbital manner, and a slider 57 is provided on a lower-end thereof.

The aforesaid slider 57 is formed by hard resin; such as, PSU, PEEK or the like. The resin of this slider 57 may be a color (such as, green or the like) which indicates, for example, a high-pressure steam sterilization countermeasure. Color is applied thereto whereby it is possible that the user can easily recognize the high-pressure steam sterilization countermeasure.

These seal member 56 and seal member 58 are provided respectively with strength reinforcements 56b and 58b, similarly to the aforementioned seal member 53. The seal members 53, 56 and 58 are elastically in intimate contact with the inner peripheral surface of the cylinder body 35 at seals 53a, 56a and 58a.

Furthermore, a cylindrical piston stopper 60 is provided on the outside of the coming-out prevention cylinder 49 at the upper end of the piston body 45 so that a flange 49a at the lower end of the coming-out prevention cylinder 49 and a flange 60a on the inner surface of the piston stopper 60 are so arranged as to be abutted against each other. An urging spring 61 which consists of a coil spring is interposed between an upper surface of the flange 60a of the piston stopper 60 and a lower surface of the presser member 50. Specifically, by a biasing force of the biasing spring 61, the presser member 50 is biased upwardly, while the piston stopper 60 is biased downwardly. Under the natural state, the flange 49a of the coming-out prevention cylinder 49 is abutted against the flange 60a of the piston stopper 60 to latch the piston body 45.

Further, a surrounding or shroud member 62 which consists of an insulation member is integrally provided on the outside of the piston stopper 60. A projection 62a on an inner surface of the shroud member 62 is engaged with an upper flange 41a of the base 41.

Moreover, an identification pin 59 is threadedly engaged with an upper end of the piston body 45. The finger application member 63 is fixedly adhered to an outer periphery of the presser member 50. The finger application member 63 has a center thereof which is provided with a leak hole 64 which is in communication with the communication passage 46 in the piston body 45. The finger application member 63 and the shroud member 62 are so arranged that, in any of the natural state and the push state of the piston 32, a gap is always maintained between the finger application 63 and an upper end of the shroud member 62.

The seal members 53, 56 and 58 and the valve body 48 are formed by natural rubber, synthetic rubber or the like. As the synthetic rubber, silicon rubber, fluoro rubber, acrylonitrile rubber, NBR or the like can be used. At this time, it is appropriate that hardness of the rubber is equal to or less than 55° in JIS-A-hardness in order to make reduction of the working capacity and seal function to be compatible with each other. In this connection, in place of the rubber, elastomers (such as, thermoplastic polyurethane or the like, or synthetic resin) may be used. It is appropriate that hardness of the elastomers and the synthetic resin is equal to or less than 55° in JIS-A-hardness, similarly to a case where the rubber is used. Moreover, materials of the plurality of respective seal members are made of different materials, whereby it is possible to improve sliding ability of the piston.

Figure 5:
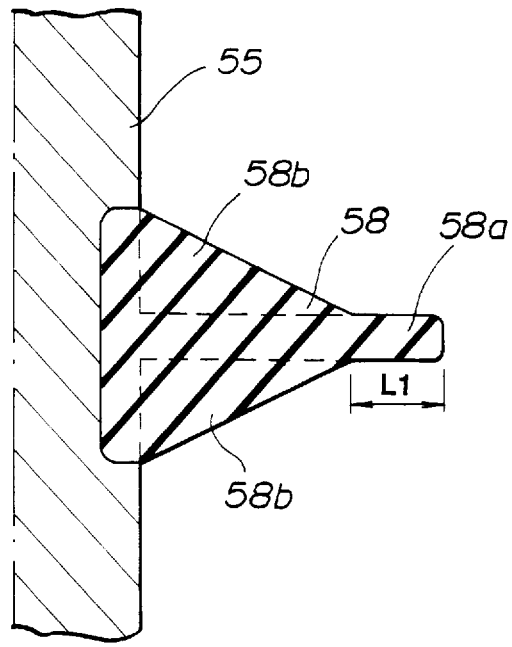
Figure 6:
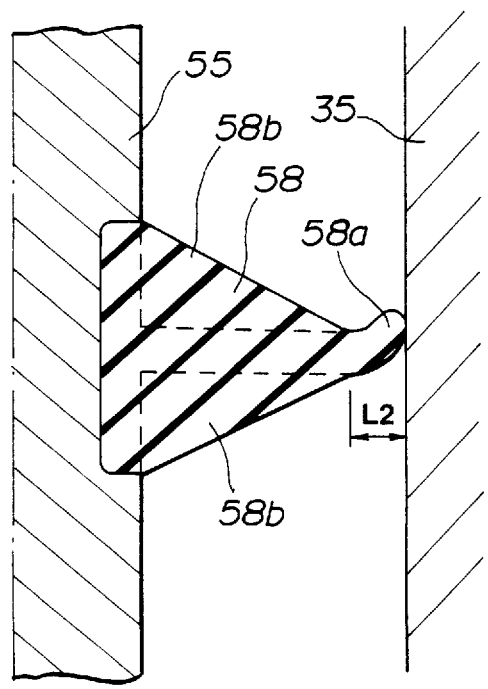

Furthermore, a color (such as, for example, red or blue) may be applied to each of the seal members. Since such color is applied thereto whereby it is possible to draw attention of the user, it is possible to find out, at once, a case where the seal members are damaged or a case where the seal members are injured or wounded In the gas-feeding and water-feeding valve 13 which is arranged in this manner, the positional relationship in the vicinity of the seal members 53, 56 and 58 in a case where the piston 32 is mounted to a predetermined position within the cylinder 31 is shown in FIGS. 5 and 6. Here, description will be made with the seal member 58 taken as an example as a representation.

The seal member 58 has the seal 58a which is such that a length thereof to the strength reinforcement 58b in a radial direction in a cross section thereof is L1 under the natural state as shown in FIG. 5. When the piston 32 is inserted into the cylinder body 35, the seal 58a is abutted against the inner wall of the cylinder body 35 as shown in FIG. 6 and is so elastically or resiliently deformed as to have a length of L2.

At this time, deformation of the seal member 58 remains only to L2 which is a scope of the seal 58a, and the elastic deformation does not reach the strength reinforcement 58b. This positional relationship is similar also to the other seal members 53 and 56.

Figure 7A:
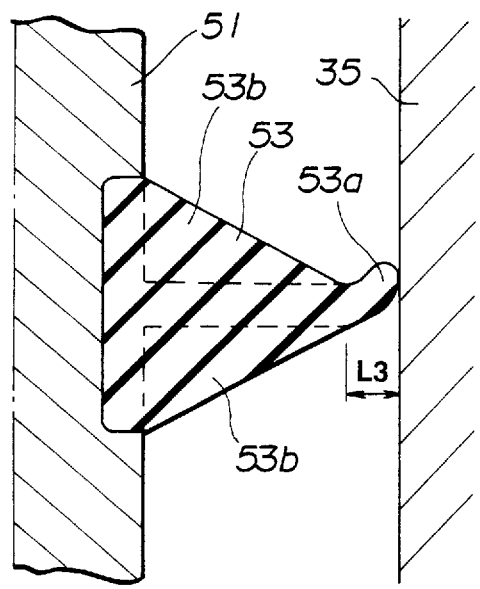
FIG. 7A is a cross-sectional view showing an amount of deformation of each of the seal members at a location where the strength reinforcement exists (an A—A cross-sectional view in FIG. 4A)
Figure 7B:
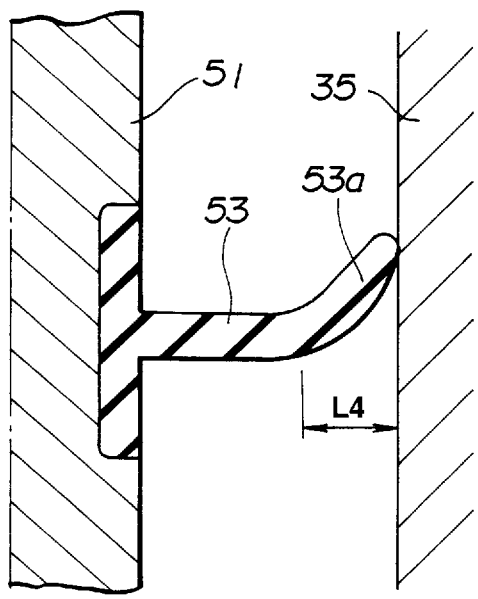
FIG. 7B is a cross-sectional view showing the amount of deformation of each of the seal members at a location where the strength reinforcement does not exist (a B—B cross-sectional view in FIG. 4A)

Here, the seal member 53 is taken as an example, and amounts of deformation of the seal 53a at a location where the strength reinforcement 53b exists and at a location where the strength reinforcement 53b does not exist are shown in FIGS. 7A and 7B. FIG. 7A is a cross-sectional view taken along a line 7A—7A in FIG. 4A, showing a cross-section of the seal member 53 at the location where the strength reinforcement 53b exists. FIG. 7B is a cross-sectional view taken along a line 7B—7B in FIG. 4A, showing a cross-section of the seal member 53 at the location where the strength reinforcement 53b does not exist.

When the seal member 53 is abutted against the inner wall of the cylinder body 35 so as to slide within the cylinder body 35, the amount of deformation of the seal 53a at the location where the strength reinforcement 53b exists becomes L3 as shown in FIG. 7A. On one hand, the amount of deformation of the seal 53a at the location where the strength reinforcement 53b does not exist becomes L4 as shown in FIG. 7B. The relationship in size or magnitude of the amounts of deformation at this time is L4>L3.

As described above, the seal 53a at the location where the strength reinforcement 53b exists is such that a sliding resistance thereof increases because the amount of deformation of the seal 53a is restricted by the strength reinforcement 53b. On one hand, the seal 53a at the location where the strength reinforcement 53b does not exist is such that the sliding resistance thereof is low because it is possible to be universally deformed. This portion is universally deformed. However, the portion is in intimate contact with the inner wall of the cylinder body 35 so as to perform function as the seal member 53.

In this manner, the strength reinforcement is provided on a part between an outer periphery of the seal member 53 and an inner periphery thereof, whereby it is possible to delete an unnecessary or useless sliding resistance. Accordingly, return response of the piston 32 is improved, and the operation capacity is also reduced.

In connection with the above, although the seal member 53 has been taken as an example, it is also possible to similary apply the above-described arrangement to the other seal members 56 and 58.

Figure 8A:
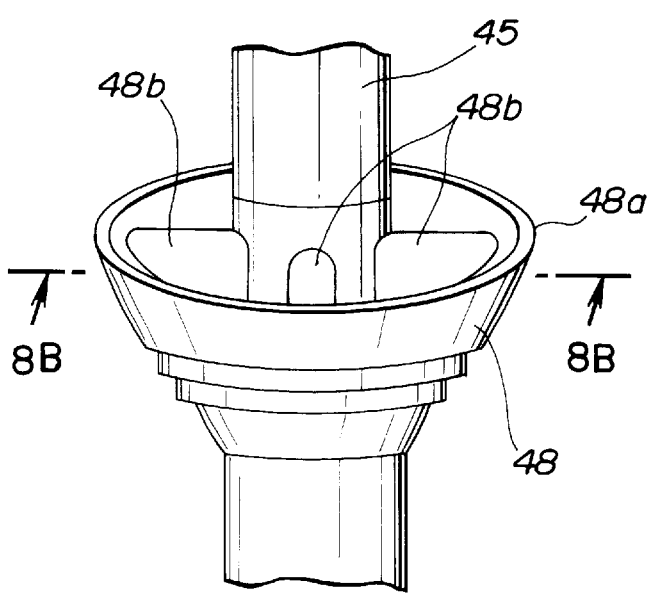
FIGS. 8A is a perspective view showing an arrangement of a valve body.
Figure 8B:
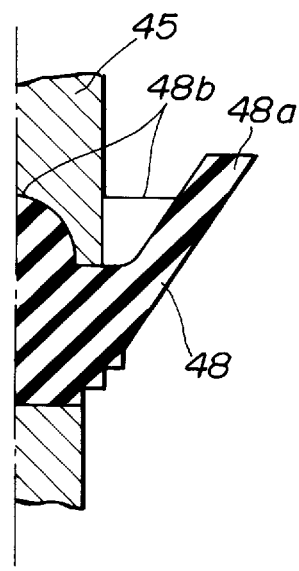
FIGS. 8B is a cross-sectional view showing the arrangement of the valve body.
Figure 9:
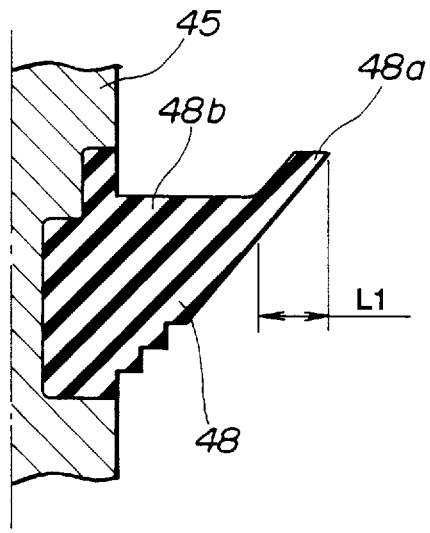

Furthermore, as shown in FIGS. 8A and 8B, in the valve body 48 which is insert-formed in the piston body 45, strength reinforcements 48b (each in the form of a rib) are also respectively provided on parts between an outer periphery of the upper surface and an inner periphery thereof. FIG. 8B is a cross-sectional view taken along a line 8B—8B in FIG. 8A. A seal 48a at the outer periphery of the valve body 48 is such that, as shown in FIGS. 9 and 10, a length of a cross-section thereof in the radial direction is L1 in the natural state similar to the seal members 53, 56 and 58. When the seal 48a at the outer periphery of the valve body 48 is inserted into the cylinder body 35, it is elastically deformed so that the length thereof becomes L2. Specifically, only the seal 48a is deformed similarly to the seam member so that the elastic deformation does not reach the strength reinforcements 48b. Further, as shown in FIG. 8B, the strength reinforcements 48b become a semicircular cross-section.

Figure 11A:
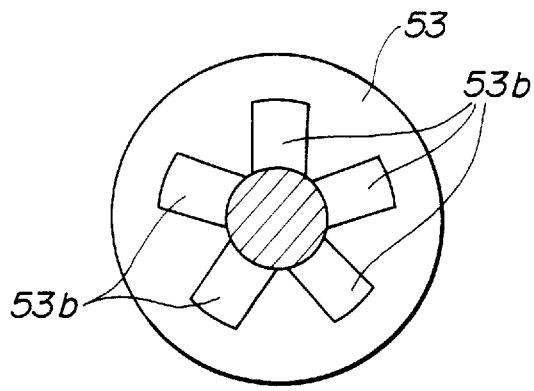
FIGS. 11A to 11E are top plan views showing modifications of an outer form of the strength reinforcement which is provided on the seal members.
Figure 11B:
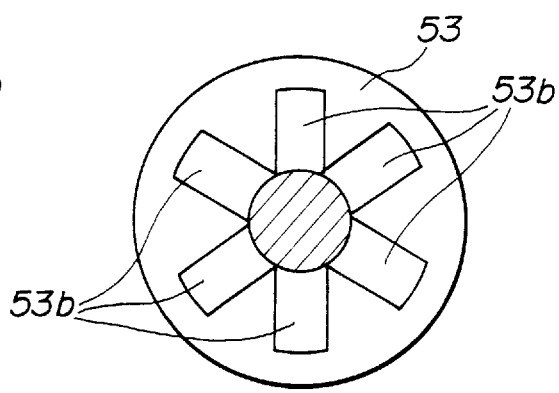

In connection with the above, as shown in FIGS. 11A and 11B, the number of the strength reinforcements 53b of the seal member 53 is not limited to the aforesaid four locations, but may be provided at five locations or six locations if the strength reinforcements 53b are provided respectively at portions which are not ranges at least adjacent to each other, of portions in which the outer periphery of the seal member 53 is divided at equal spaces or intervals. Moreover, not limited to this, if the strength reinforcements 53b are provided respectively on or at portions which are not ranges at least adjacent to each other, of portions in which the outer periphery is divided at equal spaces or intervals as described above, the number of the strength reinforcements 53b may be set optionally.

If the strength reinforcements 53b are not respectively provided at the portions which are not ranges at least adjacent to each other, of the portions in which the outer periphery of the seal member 53 is divided at equal spaces or intervals, there is a fear that deformation of the seal member becomes unequal so that sufficient seal function cannot be secured. Moreover, since, by the fact that the number of the strength reinforcements 53b increases, the strength of the seal member 53 can more increase, it is possible to reduce the dimension or size of the seal 53a to improve slidability of the piston.

Figure 11C:
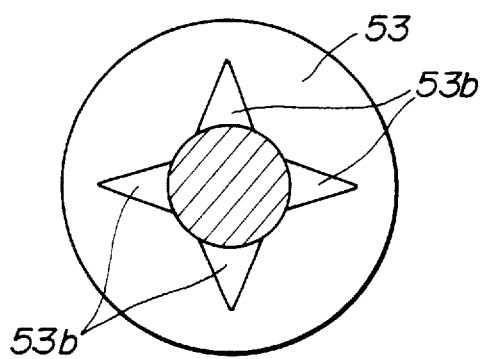
Figure 11D:
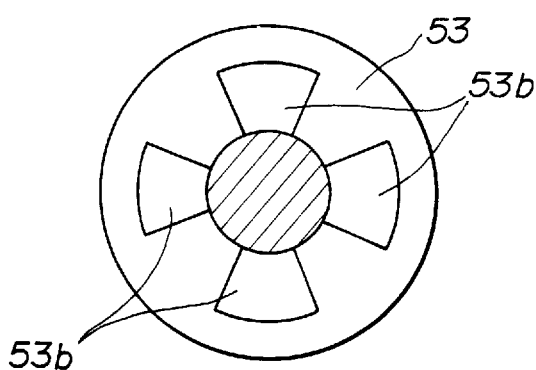

Furthermore, the form or shape of each of the strength reinforcements 53b is not limited to the aforementioned rectangular shape, but may be triangular in shape as shown in FIGS. 11C and 11D, or fun or sectorial in shape, or may be set to any optional shapes.

Figure 11E:
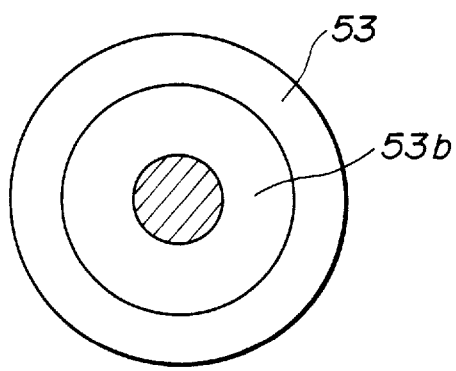

Further, as shown in FIG. 11E, the strength reinforcement 53b may be provided on the entire or whole periphery between the outer periphery of the seal member 53 and the inner periphery thereof.

Figure 12A:
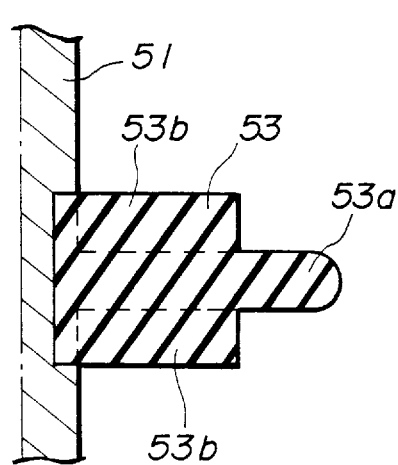
FIGS. 12A and 12B are top plan views showing modifications of a cross-sectional form of the strength reinforcement which is provided on the seal members.
Figure 12B:
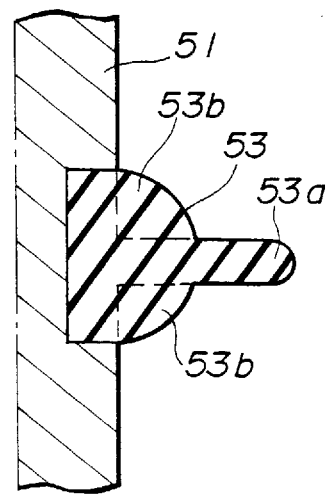

Moreover, as shown in FIGS. 12A and 12B, the cross-sectional shape of the strength reinforcements 53b is not limited to a triangular shape shown in FIG. 5, but may be a square shape or a curved shape.

A modification of these strength reinforcements can similarly be applied also to the strength reinforcements 56b and 58b of the other seal members 56 and 58.

Furthermore, in the present enforcement form, if the outer diameter of each of the seal members for water tightness is compared with the outer diameter of each of the seal members for gas tightness, the seal member for water tightness is reduced as compared with the seal member for gas tightness. This is due to reasons to be described as follows.

Air is compressive fluid, while water is non-compressive fluid. For this reason, it is necessary for a case where the water tightness is held or retained to make seal by a large or great force, as compared with a case where the gas tightness is retained. This, specifically, means that, when the piston body 45 is inserted into the cylinder body 35, it is necessary that an amount of deformation of the seal members 58 and 56 for water tightness is larger than an amount of deformation of each of the seal member 53 for gas tightness and the valve body 48. If the amount of deformation of each of the seal member 53 for gas tightness and the valve body 48 increases, the sliding capacity will increase correspondingly.

However, if the outer diameter of each of the seal member 53 for gas tightness and the valve body 48 is reduced, a circumferential length with which the cylinder body 35 and the seal member are in contact decreases. Accordingly, the outer diameter of each of the seal member 53 for gas tightness and the valve body 48 is reduced whereby it is possible to reduce the sliding capacity.

This is not limited to the strength reinforcement member which is provided with the rib, as is in the present enforcement form, but can also be applied similarly to a seal member which has no rib.

Figure 13:
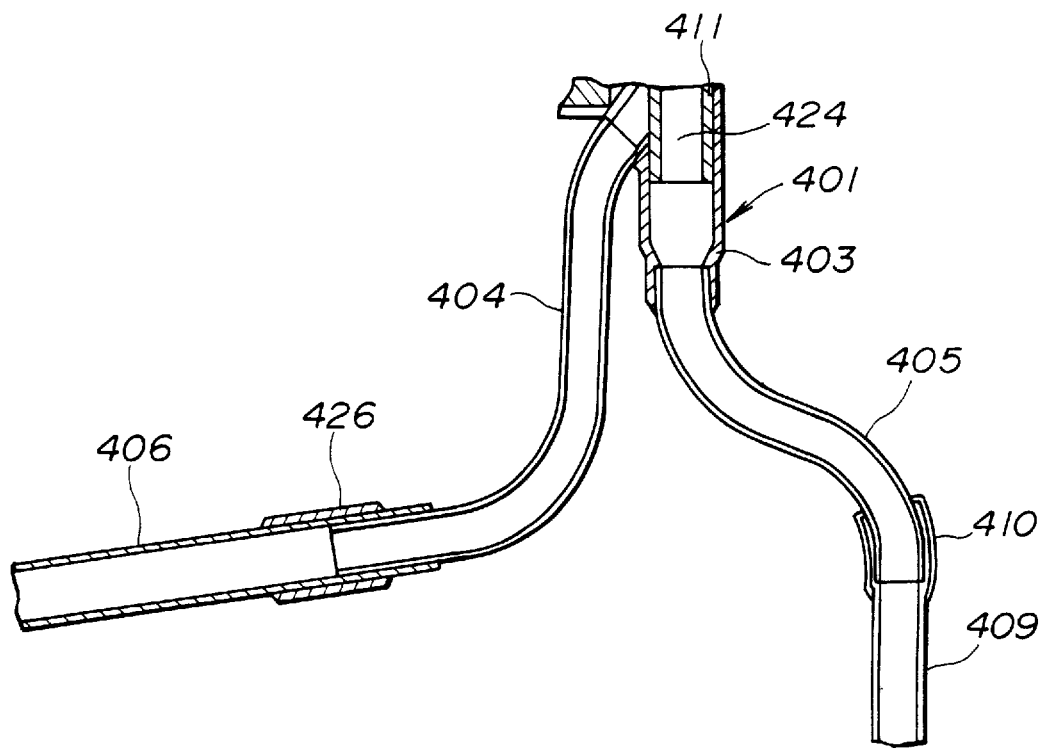
FIG. 13 is a cross-sectional view showing an arrangement of a lower part of a cylinder in the suction-line changeover device.
Figure 14:
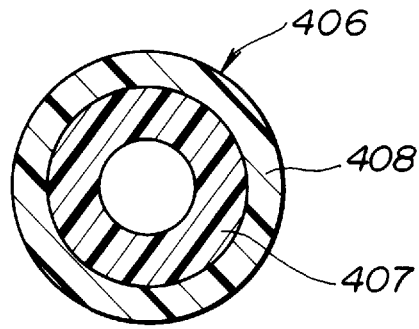
FIG. 14 is a transverse cross-sectional view showing an arrangement of a suction tube.
Figure 15:
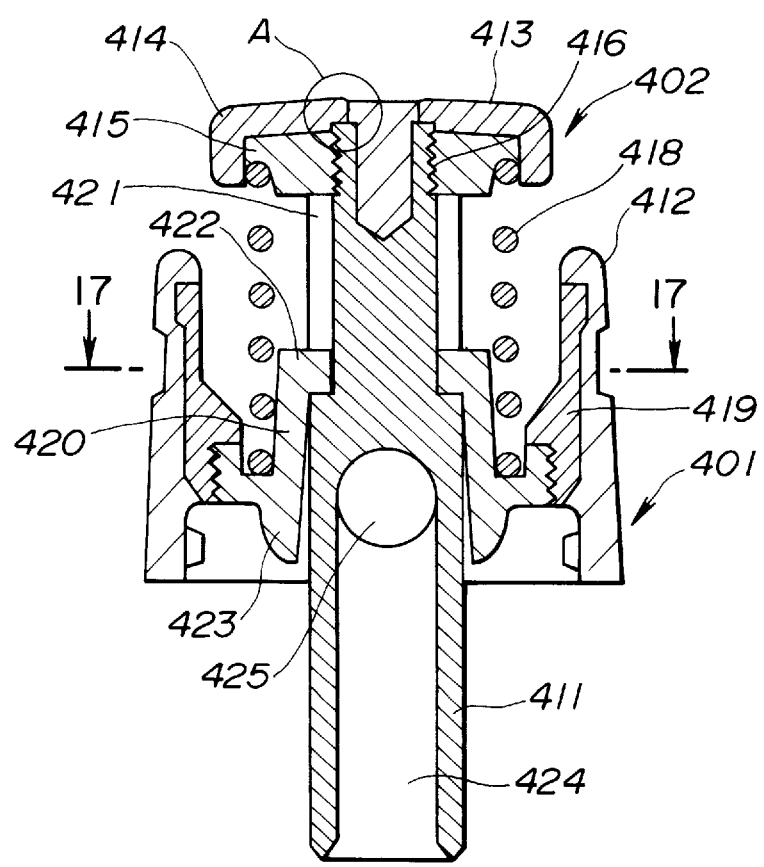
FIG. 15 is a cross-sectional view showing an arrangement of a piston in the suction-line changeover device.
Figure 16:
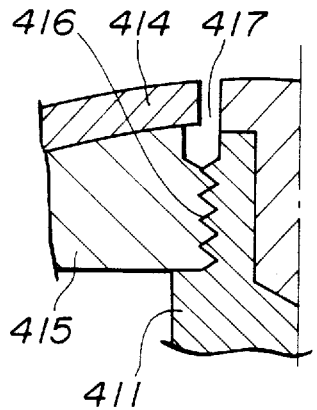
FIG. 16 is an enlarged view of a portion A in FIG. 15.
Figure 17:
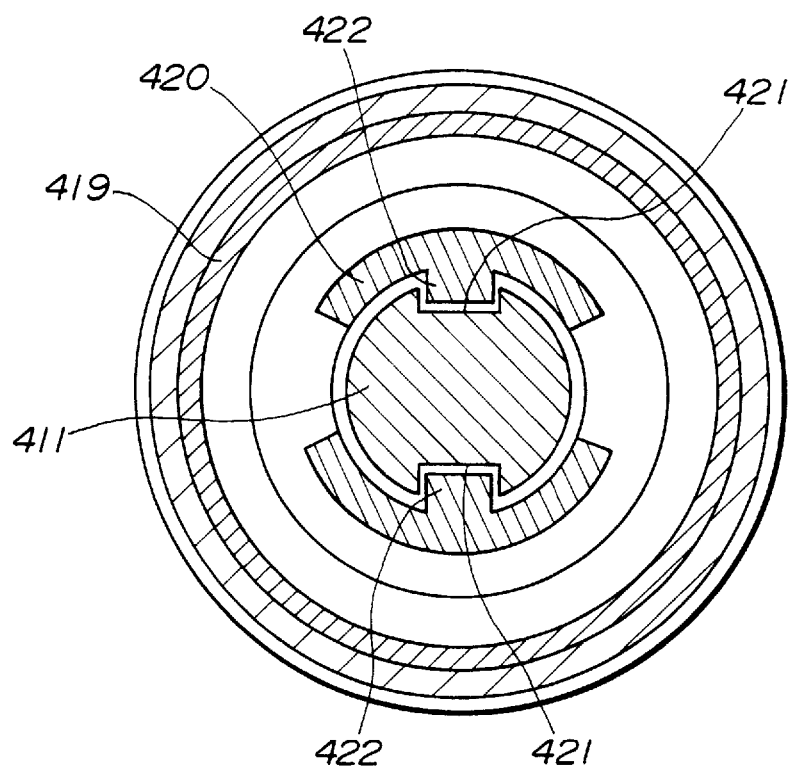
FIG. 17 is a cross-sectional view taken along a line 17—17 in FIG. 15.

Subsequently, detailed structure of the suction-line changeover device 12 which is provided in the present enforcement form is shown in FIGS. 13 to 17. FIG. 13 is a cross-sectional view showing an arrangement of a lower part of the cylinder. FIG. 14 is a transverse cross-sectional view showing an arrangement of the suction tube. FIG. 15 is a cross-sectional view showing an arrangement of the piston. FIG. 16 is an enlarged view of a portion A in FIG. 15. FIG. 17 is a cross-sectional view taken along a line B—B in FIG. 15.

The suction-line changeover device 12 comprises a cylinder 401 and a piston 402. As shown in FIG. 13, the cylinder 401 comprises three parts which include a cylinder body 403, an upstream line 404 made of a pipe made of a metal such as SUS or the like, which is connected to the cylinder body 403, and a downstream line 405. Both the upstream line 404 and the downstream line 405, which are connected to the cylinder body 403, are fixed to the cylinder body 403 by solder, adhesives or the like.

The upstream line 404 has a forward end to which a suction tube 406 is connected. A coil 426 is armored to this connection. As shown in FIG. 14, the suction tube 406 is of double-layer structure which includes an inward hard layer 407 which is formed by hard resin such as PTFE, TFE or the like and an outward soft layer 408 which is formed by resin softer than the hard layer 407. The tube of such double-layer structure is used so that buckling of the tube can be prevented from being generated when the suction tube 406 is connected to an unshown line branch on the side of the forward end, as compared to a case where a tube is used in which the entire tube is formed by hard resin (such as PTFE or the like). Thus, connection operability is improved.

The downstream line 405 has a forward end thereof to which a suction tube 409 is connected and fixed by adhesives. The suction tube 409 is formed by resin (such as, PTFE, silicon resin, vinyl chloride, polyethylene, Illux (trade mane) or the like). Adhesives are applied to an outer periphery of a connection at an end of the suction tube 409, whereby a hard quality 410 is formed. Such hard quality 410 is formed whereby advantages are attained in which adhesive strength between the downstream line 405 and the suction tube 409 is improved. Further, the hard quality 4 10 is provided up to the side lower than the end of the downstream line 405, whereby there are obtained buckling prevention advantages of the suction tube 409.

As shown in FIG. 15, the piston 402 comprises a piston body 411, a mount 412 and a cap 413. The cap 413 is such that a metallic member 415 is adhered and fixed to the inside of a cap 414, by adhesives. The metallic member 415 of the cap 413 is threadedly engaged with the piston body 411 by a threads 416. Moreover, this portion is fixed by adhesives. Fixing is performed by such adhesives so as to eliminate any fear that the cap 413 of the piston 402 becomes disassembled or dismounted during use thereof. Furthermore, in order to further raise the adhesion strength of the cap 413, an adhesive collection 417 is provided between the cap 413 and the piston body 411.

A spring 418, which is a biasing means is provided between the cap 413 and the mount 412, and the piston body 411 is upwardly biased. A pillar or column 420 is provided on the inside of the mount 412 through an insert-member 419. The piston body 411 has a lower part thereof which is inserted and passes through an insertion hole at the center of the pillar 420.

A groove 421 is provided in a side surface of the piston body 411 in a longitudinal direction. A stopper 422 which is provided in projection on the inside of an upper end of the pillar 420 is engaged with the groove 421. As shown in FIG. 17, the pillar 420 is formed in the form of an arc so as to contain the stopper 422 along the outer periphery of the piston body 411. Thus, the strength of the stopper 422 is sufficiently secured.

When the piston 402, which is arranged in this manner, is mounted to the cylinder 401, a fixture 423 which is provided in projection on a lower part of the pillar 420 is fitted into an unshown fixing hole which is provided in an upper part of the cylinder body 403, and is fixed thereto. Thus, the piston 402 is so mounted as to be slidable within the cylinder body 403.

Under such a condition, the piston 402 is pressed whereby the downstream line 405 is in communication with a communication passage 424, a side-surface communication passage 425 and the upstream line 404 which are formed within the piston body 411. Suction is performed from the upstream line 404 toward the downstream line 405 by a suction pump which is connected to the downstream line 405.

Subsequently, function of the gas-feeding and water-feeding valve 13 according to the present enforcement form will be described.

Figure 2:
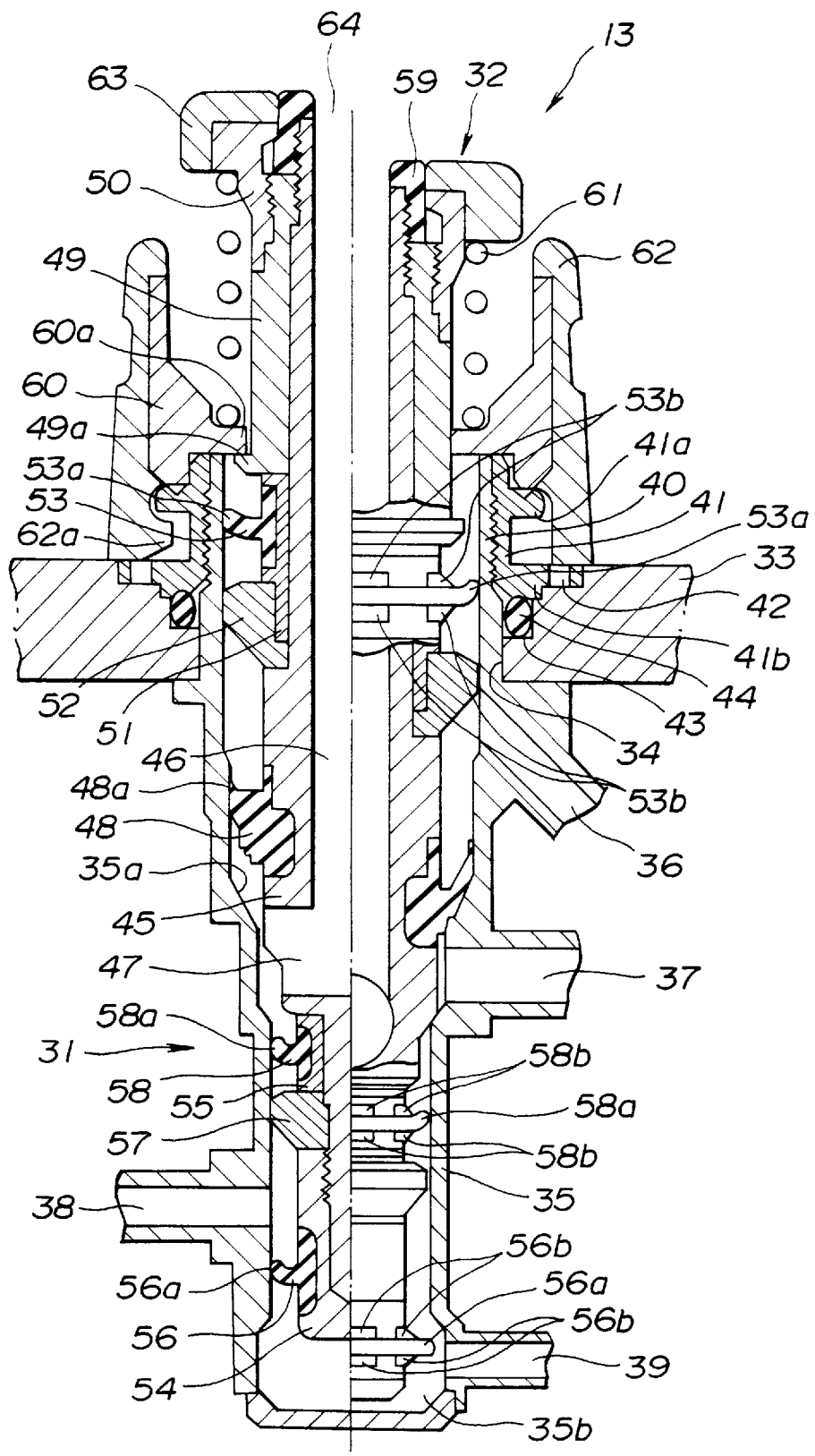

As shown on the left in FIG. 2, under the natural state, the piston body 45 is pushed upwardly by a biasing force of the biasing spring 61. A location between the water-feeding line 38 and the water-feeding line 39 is cut off by a seal 56a of the seal member 56 on the lower side. Flow of the fluid which is sent out from the water-feeding tank 19 and which flows toward the water-feeding line 38 from the water-feeding line 39 is cut off.

Moreover, the gas which flows through a flow passage within the cylinder body 35, which is defined by the seal 58a of the intermediate seal member 58 and the seal 48a of the valve body 48, and which is sent out from the pump within the light source device 5 flows through the gas feeding line 37, and flows into the opening 47 which is located at the side surface of the piston body 45. The gas flows through the communication passage 46 in the piston body 45, and flows out to the atmosphere from the leak hole 64 in the finger application member 63.

Under this natural state, if the operator applies his or her finger to the leak hole 64 in the finger application member 63 to close the same, the valve body 48 is bent inwardly by the sending-out pressure of the gas from the light source device 5, and the seal 48a is spaced away from the inner wall surface of the cylinder body 35. As a result, the gas which flows in from the gas feeding line 37 flows through a flow passage within the cylinder body 35, which is defined by a seal 58a of the intermediate seal member 58 and the seal 53a of the upward seal member 53, and flows out from the gas-feeding line 36. Thus, gas feeding is performed from the gas-feeding and water-feeding nozzle at the forward end of the insertion.

As shown on the right in FIG. 2, under a state in which the finger application member 63 is pushed by the finger, and the piston body 45 is pressed against the biasing force of the biasing spring 61, if the finger is applied to the leak hole 64 to close the same, a seal 48a of the valve body 48 is urged against a tapering surface 35a of the cylinder body 35. A location with respect to the seal 58a of the intermediate seal member 58 becomes air tightness. In the gas from the light source device 5, flow passage is cut off.

At this time, the seal 56a of the downward seal member 56 is moved to a large diameter 35b on the downward side of the cylinder body 35. Thus, a gap is defined with respect to the inner wall surface of the cylinder body 35. As a result, the liquid which flows in from the water-feeding line 39 flows through the flow passage within the cylinder body 35 which is defined by the seal 58a of the intermediate seal member 58, and flows out from the water-feeding line 38. Thus, water feeding is performed from the gas-feeding and water-feeding nozzle at the forward end of the insertion.

As described above, according to the arrangement of the present enforcement form, the arrangement is such that the seal at the outer periphery of the seal member is reduced in thickness to reduce the deformation of the deformation, and the seal member is deformed by a small or low force. With such arrangement, the capacity which is required for the sliding movement of the piston is reduced, and the strength reinforcement is provided on a part of the seal member (the inner diameter other than the deformation) to keep the strength with respect to the movable direction of the seal member. Consequently, deformation of the seal member due to the sliding resistance of the piston is prevented from occurring; thus, water tightness and the gas tightness within the cylinder can be maintained, and the sliding resistance of the piston can be adequately kept without the use of lubricating oil. In this manner, it is possible to improve sliding ability between the cylinder and the piston at the time of operation of the operation button. Thus, it is possible to make operability of the line changeover device superior. Since it is possible to facilitate also handling at the time of cleaning, labor or trouble of the user is reduced.

FIGS. 18 to 25 show a second enforcement form of the present invention.

The second enforcement form is arranged such that, in the gas-feeding and water-feeding line changeover device, sizes or the magnitudes of the strength reinforcements which are provided on the seal member are different from each other in upper and lower surfaces. Here, two arrangement examples are shown as a modification of the seal members 53, 56 and 58, which are provided on the piston body 45 and have been described in the first enforcement form. An arrangement of the other portions of the gas-feeding and water-feeding line changeover device is similar to that of the first enforcement form. Here, only an arrangement of the seal member will be described.

Figure 18:
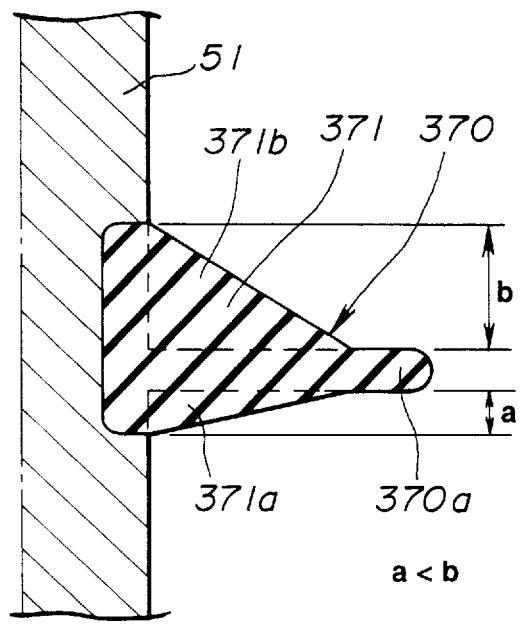

As shown in FIG. 18, a seal member 370 is provided, in the orbital form, on the side of the seal support member 51 which is fixed to the piston body 45. The seal member 370 is so arranged as to have ribs 371 as strength reinforcements every predetermined intervals between an outer periphery thereof and an inner periphery thereof. In the first arrangement example, the ribs 371 are different in height from each other in the upward side and the downward side in a seal 370a. Specifically, it is assumed that the height of an upward rib 371b which is located above the seal 370a of the seal member 370 is b, while the height of a downward rib 371a which is located below the seal 370a is a. Then, the heights of a and b are a<b. The height of the upward rib 371b is formed higher.

Figures 19A, 19B:
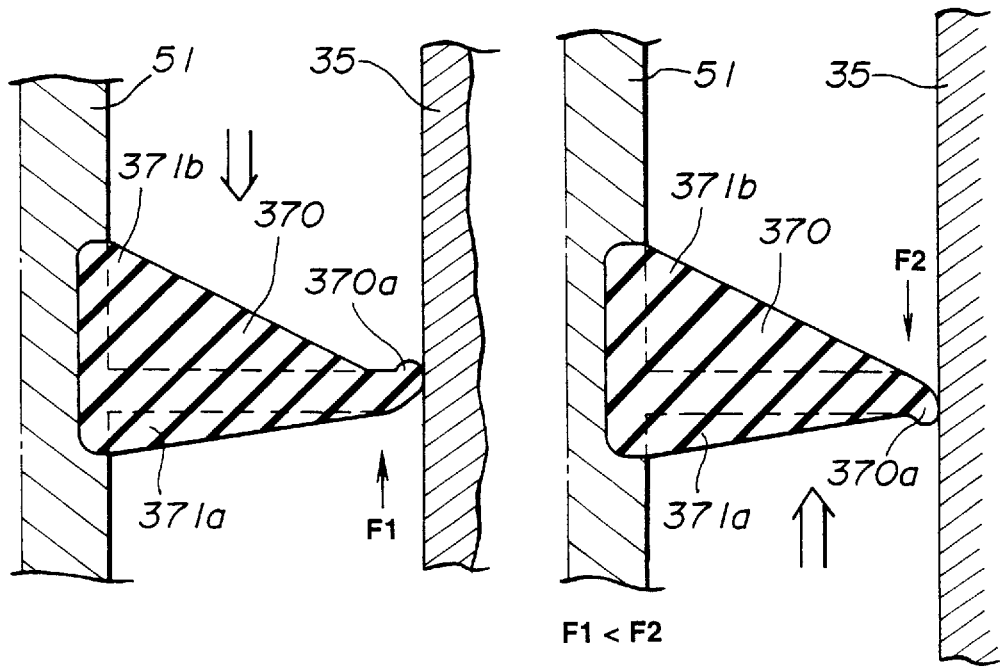
FIGS. 19A and 19B are cross-sectional views showing a deformed state of each of the seal members at the time of sliding within the cylinder in the first arrangement example.

Function at the time the seal member 370 arranged in this manner operates will be described. When the piston 32 of the gas-feeding and water-feeding valve 13 is so operated as to be pressed within the cylinder part 35 of the cylinder 31, as shown in FIG. 19A, the seal 370a of the seal member 370 is upwardly deformed by the sliding resistance with respect to the wall surface of the cylinder body 35. At this time, a reaction or a drag F1, which prevents the seal 370a from being deformed, acts from the downward rib 371a.

Further, when the piston 32 is returned upwardly, the seal 370a of the seal member 370 is deformed downwardly by the sliding resistance with respect to the wall surface of the cylinder body 35, as shown in FIG. 19B. At this time, a drag F2 which intends to prevent deformation of the seal 370a acts from the upward rib 371b.

Since the upward rib 371b and the downward rib 371a are different in size from each other as described previously, the relationship in magnitude between the drag F1 and the drag F2 is F1<F2. For this reason, when the piston 32 is so operated as to be pushed, the sliding resistance is reduced less than that at the time returned to the original state. Since the seal 370a of the seal member 370 is deformed smoothly, it is possible to reduce or lighten the capacity at the time of push operation.

This can similarly be said with respect to all the seal members which are provided on the piston body 45. Accordingly, in order to further reduce the push operation capacity, the plurality of seal members should be made to a similar structure. Moreover, in order to obtain the necessary or required push operation capacity, this structure may be applied only to partial seal members of the seal members which are provided in plural.

Figure 20:
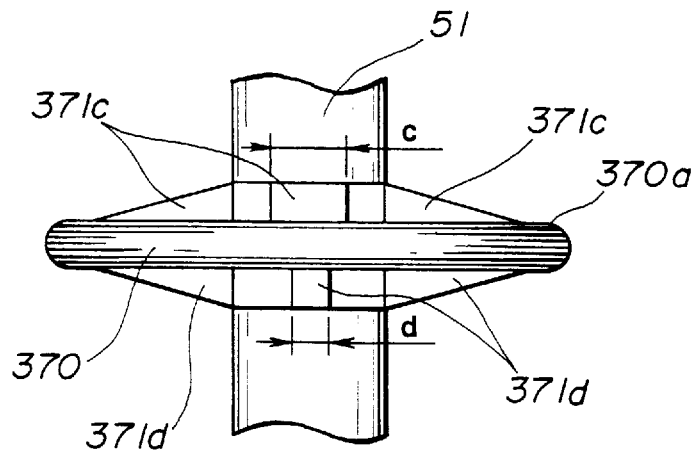

In connection with the above, advantages similar to those of the first arrangement example can be obtained also in a case where, as shown in FIG. 20, the arrangement is such that upward ribs 371c and downward ribs 371d which are different in width from each other are provided above and below the seal member 370, and c>d is obtained when the width c of each of the upward ribs 371c and the width d of each of the downward ribs 371d are compared with each other.

Figure 21:
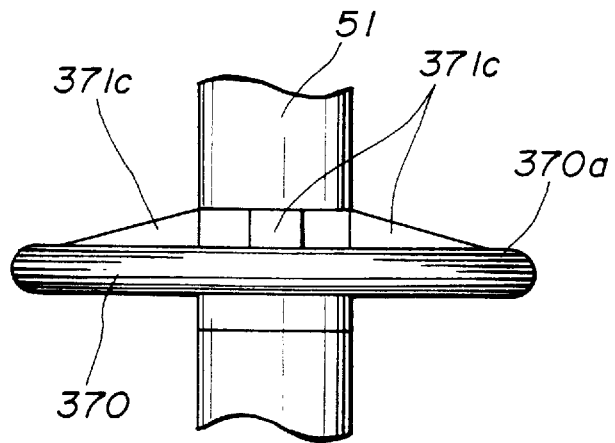

Furthermore, as shown in FIG. 21, similar advantages are also obtained if the upward ribs 371c are provided only on the upper side of the seal member 370.

Figure 22:
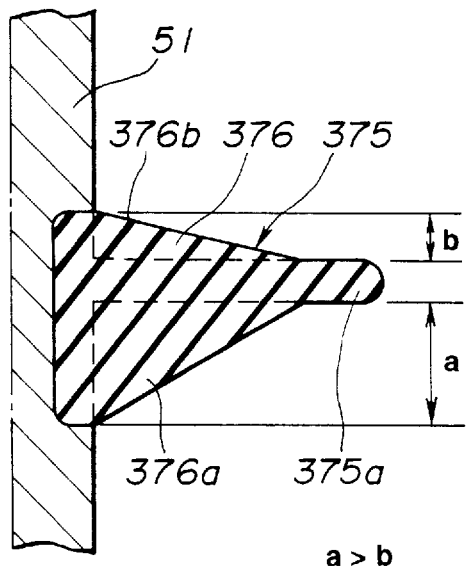

A seal member 375 of the second arrangement example shown in FIG. 22 is such that, similar to the first arrangement example, an upper side and a down side of a rib 376 are different in height from each other. However, in contrary to the first arrangement example, if it is assumed that a height of an upward rib 376b which is located at an upper side of a seal 375a is b, and a height of a downward rib 376a which is located at the lower side of the seal 375a is a, the heights of a and b are a>b. The height of the downward rib 376a is formed higher.

Figure 23A:
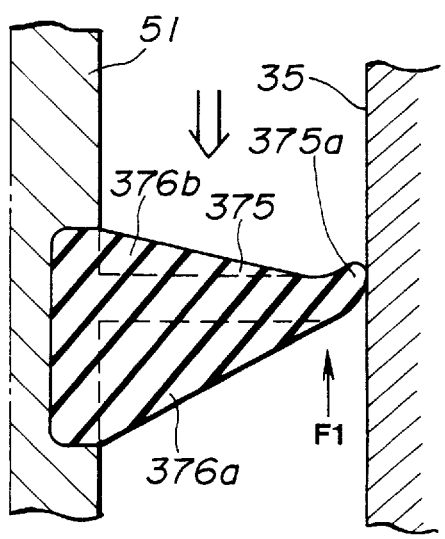
FIGS. 23A and 23B are cross-sectional views showing a deformed state of each of the seal members at the time of sliding within the cylinder in the second arrangement example.
Figure 23B:
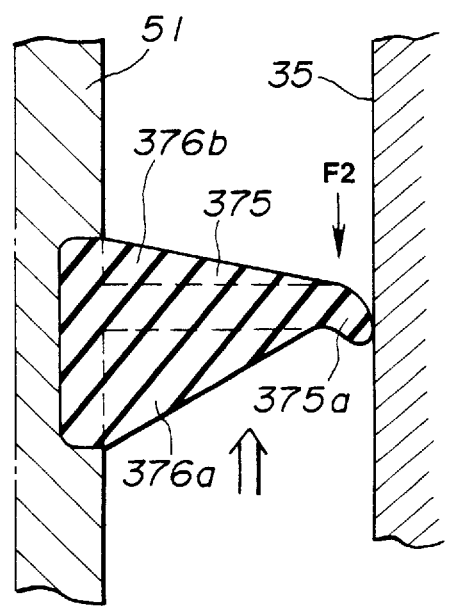

In this case, as shown in FIGS. 23A and 23B, the relationship in magnitude between the drag F1 which acts from the downward rib 376a with respect to the deformation of the seal 375a when the piston 32 is operated in pushing and the drag F2 which acts from the upward rib 376b when the piston 32 is returned upwardly is F1>F2. For this reason, when the piston 32 is returned to the original state, the sliding resistance is reduced less than that when the piston 32 is operated in pushing. Since the seal 375a of the seal member 375 is deformed smoothly, it is possible to improve the response at the time the piston 32 is returned.

This can similarly be said with respect to all the seal members which are provided on the piston body 45. Accordingly, in order to further fasten the response at the time of returning of the piston, all the plurality of seal members should be made to a similar structure. Further, this structure is applied to partial seal members of the seal members which are provided in plural, whereby it is also possible to set the response at the time of returning of the piston to an optional level.

Figure 24:
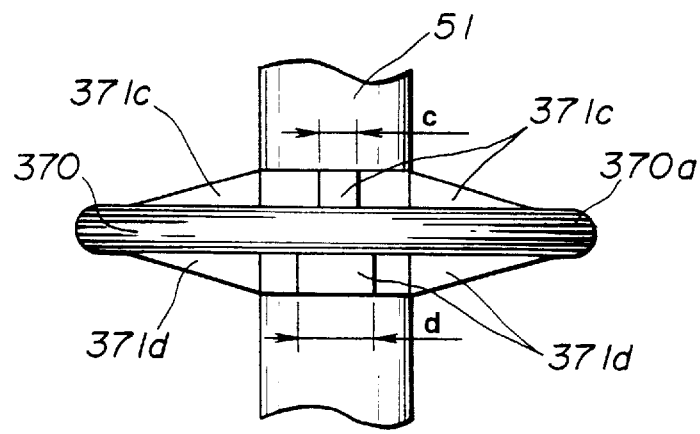

In connection with the above, advantages similar to those of the second arrangement example can also be obtained in a case of an arrangement in which, as shown in FIG. 24, the upward ribs 371c and the downward ribs 371d which are different in width from each other are provided respectively above and below the seal member 370, and d>c is obtained when the width c of each of the upward ribs 371c and the width d of each of the downward ribs 371d are compared with each other.

Figure 25:
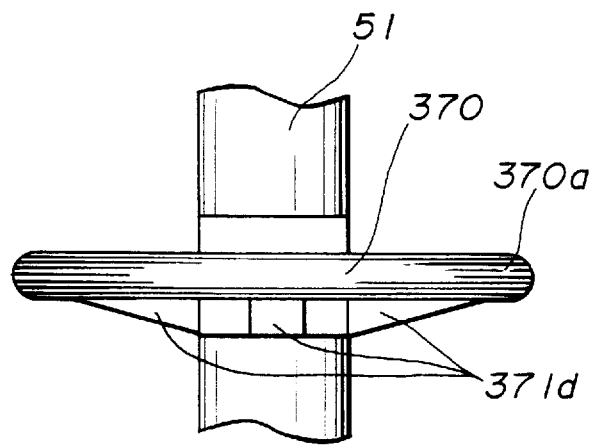

Furthermore, as shown in FIG. 25, similar advantages are also obtained if the downward ribs 371d are provided only on the lower side of the seal member 370.

Further, it is also possible that the relationships in size between the upward ribs 371b and 376b and the downward ribs 371a and 376a are optionally combined with each other among the plurality of seal members 53, 56 and 58 which are provided on the gas-feeding and water-feeding line changeover device. Thus, it is possible to provide the gas-feeding and water-feeding line changeover device which has the sliding characteristics, and which is suited for or in conformity with the like of the user.

As described above, the sizes or magnitudes of the ribs, which are provided on the upper and lower surfaces of the seal member, are different from each other in the upward and the downward, whereby it is made possible to optionally set the pushing operation capacity, the return response, and the slidability, in accordance with the like of the user, at the time of push operation of the piston and at the time of returning thereof A third enforcement form of the present invention is shown in FIGS. 26A and 26B and FIGS. 27 and 28.

The third enforcement form is arranged such that arrangements of the strength reinforcements which are provided on the seal member in the gas-feeding and water-feeding line changeover device are different in upper and lower surfaces from each other. Here, an example of the modification of the seal members 53, 56 and 58, which are provided on the piston body 45 and described in the first enforcement form, is shown. An arrangement of the other portions of the gas-feeding and water-feeding line changeover device is similar to that of the first enforcement form. Here, only the arrangement of the seal member will be described.

Figure 26A:
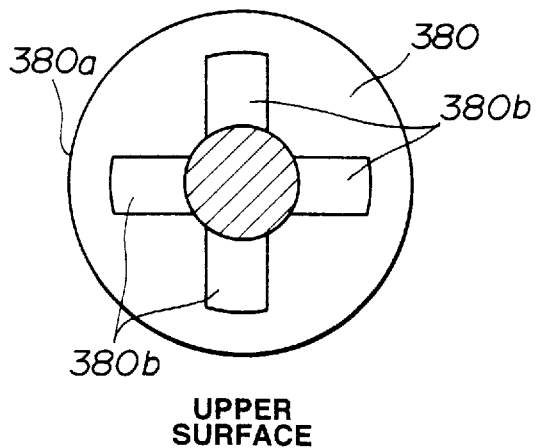
FIGS. 26A, 26B, 27 and 28 relate to a third enforcement form of the present invention.
Figure 26B:
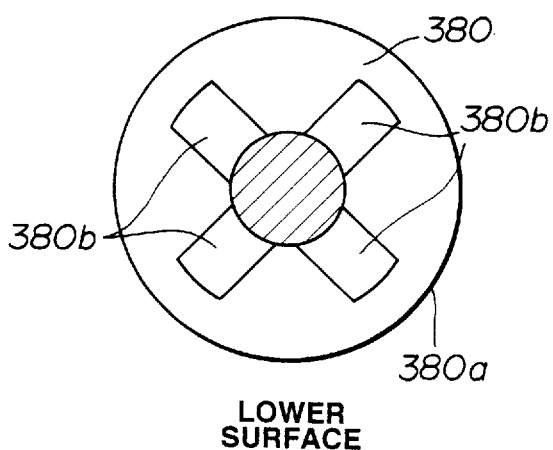

As shown in FIGS. 26A and 26B, a seal member 380 generally in the form of a disk which is provided on the piston body 45 is so arranged as to have ribs 380b as strength reinforcements every predetermined intervals between an outer periphery thereof and an inner periphery thereof. In the present enforcement form, the ribs 380b are provided respectively at positions which are different from each other in the upper surface of the seal member and the lower surface thereof. Specifically, the ribs 380b are provided at four locations on each of the upper surface and the lower surface of the seal member 380 every 90°. The upward ribs and the downward ribs are arranged at an angle of 45° from each other.

In connection with the above, in a case where the ribs 380b, for example, are provided respectively at six locations on each of the upper and lower surfaces every 60°, an angle which is defined between the upward and downward ribs becomes 30°. Accordingly, even if the number of the arranged ribs varies, the angles which are defined by the ribs on the upper and lower surfaces are equal to each other.

The ribs 380b are provided in such positional relationship, whereby, when the seal member 380 slides within the cylinder body 35, it is possible to reduce the sliding resistance.

Figure 27:
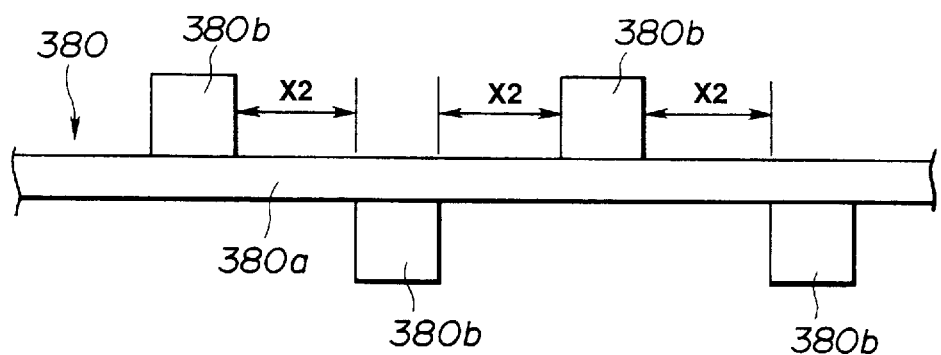
Figure 28:
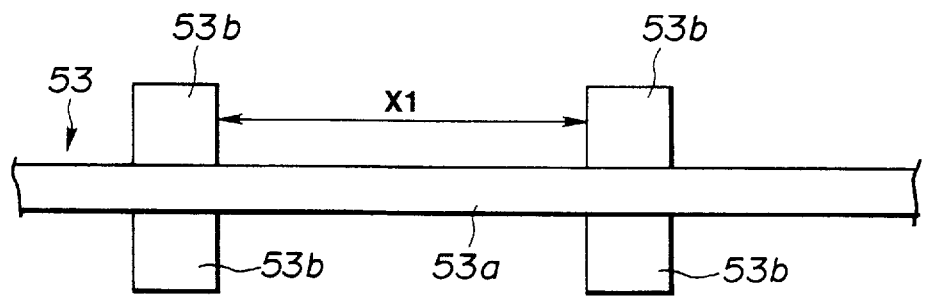

Development views of the strength reinforcement 53b of the seal member 53 in the aforesaid first enforcement form and the ribs 380b of the seal member 380 in the present enforcement form are shown respectively in FIGS. 27 and 28. Like FIG. 28, in a case where the strength reinforcements 53b are located at the same position of both the upper and lower surfaces with the seal 53a put therebetween, a space or interval X1 of the seals 53a between the strength reinforcements 53b is made larger than an interval X2 of a seal 380a between the ribs 380b, as compared with a case where, as shown in FIG. 27, the ribs 380b are arranged alternately on the upper and lower surfaces with the seal 380a put therebetween. For this reason, it can be said that, in the amount of deformation of the seal at the time of sliding of the piston, a case of FIG. 28 becomes larger than a case of FIG. 27.

Like FIG. 27, when the position of the rib 380b is shifted in the upper and lower surfaces of the seal member 380, reinforced locations increase as compared with the seal member 53 in FIG. 28. For this reason, in the seal member 380 of the third enforcement form, if the ribs 380b which are provided upper and lower are made to ones smaller than the strength reinforcement 53b of the seal member 53 in the first enforcement form, the strength securement in order to prevent the seal member from being deformed is made possible. In this case, since the ribs 380b are smaller than the strength reinforcement 53b, deformation of the seal 380a at the time the seal member 380 slides is made easier than the seal 53a in the first enforcement form.

Accordingly, the ribs 380b are arranged such that the positions thereof are so shifted as to be different from each other in the upper and lower surfaces, as is in the present enforcement form, whereby it is possible to reduce the resistance at the time of sliding as compared with a case where the ribs are provided at the same position of both the upper and lower surfaces. Thus, it is possible to improve the slidability while the necessary strength of the whole seal member is secured. It is possible to provide the gas-feeding and water-feeding line changeover device in which the sliding resistance is small or low, the response is superior, and the operability is superior.

Figure 29:
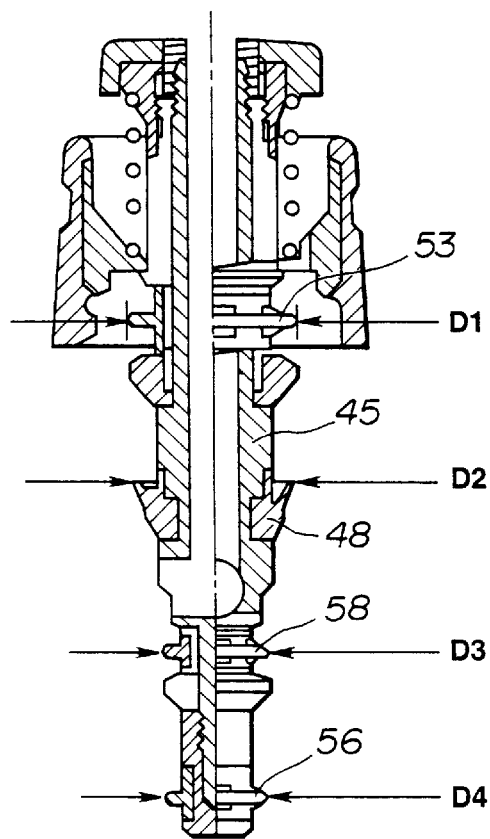
FIG. 29 is an explanatory view showing each of the seal members which are provided on the piston, and the positional relationship between a valve body and a cylinder of a cylinder part.
Figure 29:
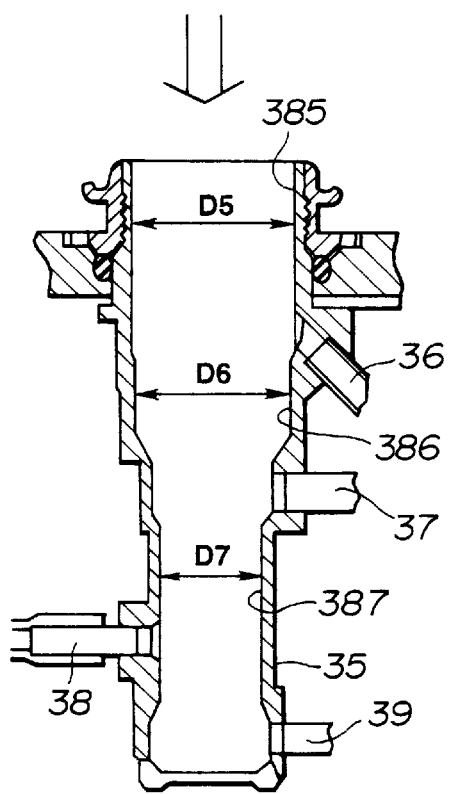

Subsequently, the positional relationship between the seal members 53, 56 and 58 and the valve body 48 which are provided on the piston 32, and the cylinder body 35 of the cylinder 31 will be described with reference to FIG. 29.

In a prior-art gas-feeding and water-feeding line changeover device, sufficient consideration has not been paid with respect to the relationship between the outer diameter of the seal member and the inner diameter of the cylinder. Depending upon the size setting, there was a fear that the slidability of the piston will be hurt or injured by the amount of deformation of the seal member, more than the necessity.

In view of the above, the amount of deformation of the seal member at the time the seal member is inserted and passes into the cylinder is made to an optimum value, whereby it is possible to improve the slidability of the piston while securing more certain water tightness and gas tightness. Thus, the gas-feeding and water-feeding line changeover device which is high in operability is arranged.

In the present enforcement form, the seals of the seal members which are provided in plural are all in the form of a ring. In these seal members, the lower or the smaller the amount of deformation of the seals, the lower or the smaller the frictional force which is generated between the cylinder and the seal members. Accordingly, the slidability of the seal members is improved.

In the present enforcement form, the relationship to be hereinafter described holds between the seal member for securing the gas tightness and the seal member for securing the water tightness, and the cylinder.

Specifically, it is assumed that an outer diameter of the seal member 53 is D1, an outer diameter of the valve body 48 is D2, an outer diameter of the seal member 58 is D3, an outer diameter of the seal member 56 is D4, an inner diameter of a gas-tightness packing slide 385 of the cylinder body 35 is D5, an outer diameter of a valve-body slide 386 is D6, and an outer diameter of a water-tightness packing slide 387 is D7. Then, the relationship between the amounts of deformation A1 and A2 of the seal member 53 for gas tightness and the valve body 48 and the amounts of deformation W1 and W2 of the respective seal members 58 and 56 for water tightness is shown by the following equations:

A1=(D1−D5)
A2=(D2−D6)
W1=(D3−D7)
W2=(D4−D7)

At this time, the following relationship holds between An and Wn (n=1, 2):

$$An < Wn \ (n=1, 2)$$

The seal member 53 and the valve body 48 are provided for securing the gas tightness, in order to perform sealing of the air which flows between the gas-feeding line 36 and the gas-feeding line 37. On one hand, the seal members 58 and 56 are provided for securing the water tightness, in order to perform sealing so that water flowing between the water-feeding line 38 and the water-feeding line 39 does not leak outside. Since the air is compressive fluid, while the water is non-compressive fluid, a larger force will be necessary in order to secure the water tightness. Accordingly, it is possible to reduce the amounts of deformation of the seal member 53 and the valve body 48 lower or smaller than the amounts of deformation of the seal members 58 and 56.

In view of the above, in the present enforcement form, the amounts of deformation A1 and A2 of the seal member 53 for gas tightness and the valve body 48 are set small as compared with the amounts of deformation W1 and W2 of the seal members 58 and 56 for water tightness, whereby it is possible to reduce the sliding resistance of the seal member for gas tightness, as compared with a case where the amounts of deformation of the seal members 53, 56 and 58 and the valve body 48 are all made to the same. Thus, since the sliding resistance of the piston can be reduced, it is possible to improve the slidability of the piston.

By the fact that the rubber harnesses of the plurality of respective seal members are differentiated from each other, it is possible to improve the slidability of the piston. For example, by the fact that the rubber hardness of the seal member for gas tightness is made lower than the rubber hardness of the seal member for water tightness, the sliding resistance of the seal member for gas tightness is reduced, and it is possible to reduce the sliding resistance of the piston. Thus, it is possible to improve the slidability of the piston.

In connection with the above, also in this structure, the structure in which the positions of the strength reinforcements are so arranged as to be shifted in the upper and lower surfaces as shown in the third enforcement form is further applied so that it is also possible to further reduce the sliding resistance.

Figure 30:
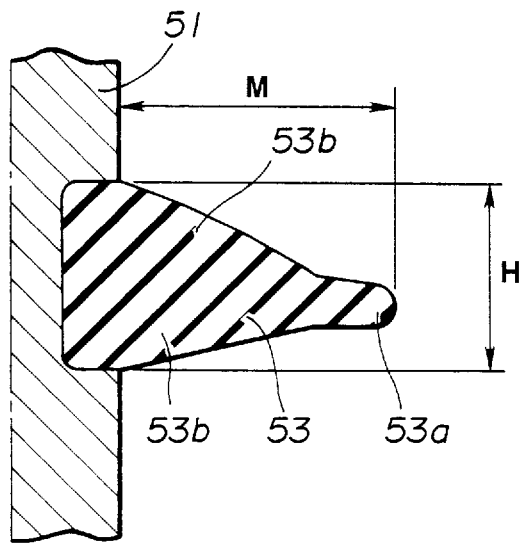
FIG. 30 is an explanatory view showing the relationship of a width and a height of each of the seal members which are provided on the piston.

Moreover, the relationship between the width and the height of each of the seal members 53, 56 and 58 which are provided on the piston 32 will be described with reference to FIG. 30. The seal member 53 is shown in FIG. 30 as representation.

In spite of the fact that, generally, there are ribs that are the strength reinforcements, the seal member 53 is such that the sliding resistance is reduced if the relationship between the width M and the height H is M<H. In view of this, setting is made such that the width M and the height H is so set as to be M<H, whereby it is possible to reduce the sliding resistance.

Furthermore, the smaller the amount of deformation $\Delta L = (L1-L2)$ of the seal 58a of the seal member 58 shown in FIGS. 5 and 6, the sliding resistance is also reduced. Accordingly, the magnitude of the rib is regulated to reduce the amount of deformation of the seal, whereby the sliding resistance can further be reduced.

Figure 31:
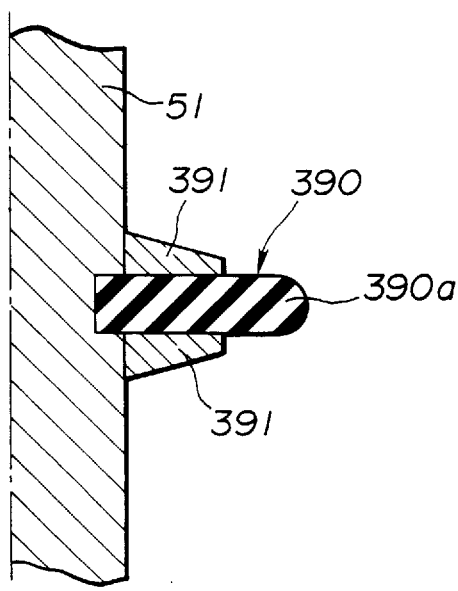
FIG. 31 is a cross-sectional view showing an arrangement of each of seal members relating to a fourth enforcement form of the present invention.

A fourth enforcement form of the present invention is shown in FIG. 31. The fourth enforcement form is an example in which, in the gas-feeding and water-feeding line changeover device, the seal of the seal member and the strength reinforcements are formed respectively by different materials. An arrangement of the other portions, except for the seal member, is similar to that in the first enforcement form. Here, only an arrangement of the seal member will be described.

A seal member 390 is formed by a seal 390a generally in the form of a disk, consisting of an elastic body such as silicon rubber or the like, and strength reinforcements 391 which consist of a metal (such as, stainless steel or the like), or resin which bears up against heat which is generated at the time of rubber forming (such as, PEEK (polyether ether ketone) or the like).

The seal 390a is so provided as to be insert-formed in the strength reinforcements 391, or is adhered and fixed to the same. The strength reinforcements 391 are adhered and fixed to the seal support member 51. In this connection, the strength reinforcements 391 may be so formed as to be adhered and fixed to the seal 390a and the seal support member 51, after the seal 390a has been insert-formed on the seal support member 51.

In the present enforcement form, since the seal 390a and the strength reinforcements 391 are made respectively to materials different from each other, it is possible to sufficiently secure the strength of the strength reinforcements 391 with respect to the deformation of the seal 390a. Accordingly, the size of the seal 390a can be reduced while preventing excessive deformation of the seal member 390. For this reason, the frictional force between the seal 390a and the cylinder body 35 can be reduced, making it possible that the slidability of the piston is improved.

The arrangement of the seal member 390 in the present enforcement form can be applied also to any of the seal members 53, 56 and 58 in the first enforcement form.

In connection with the above, in the arrangement example in FIG. 31, the strength reinforcements 391 are provided respectively on the upper side of the seal member 390 and on the lower side thereof. However, the strength reinforcements 391 may be provided only on the upper side of the seal member 390 or on the lower side thereof.

As described above, according to each of the enforcement forms of the present invention, the strength of the seal member provided around the piston, with respect to the movable direction, is kept, and deformation due to the sliding resistance of the piston is prevented so that the water tightness and the gas tightness within the cylinder can be held or retained. The sliding resistance of the piston is adequately kept without the use of the lubricating oil so that it is possible to improve the slidability between the cylinder and the piston at the time of operation. Thus, there are advantages derived from such structural arrangements in that it is possible to provide the line changeover device for the endoscope, which is superior in operability, and is also easy in handling at the time of cleaning.

Figure 32:
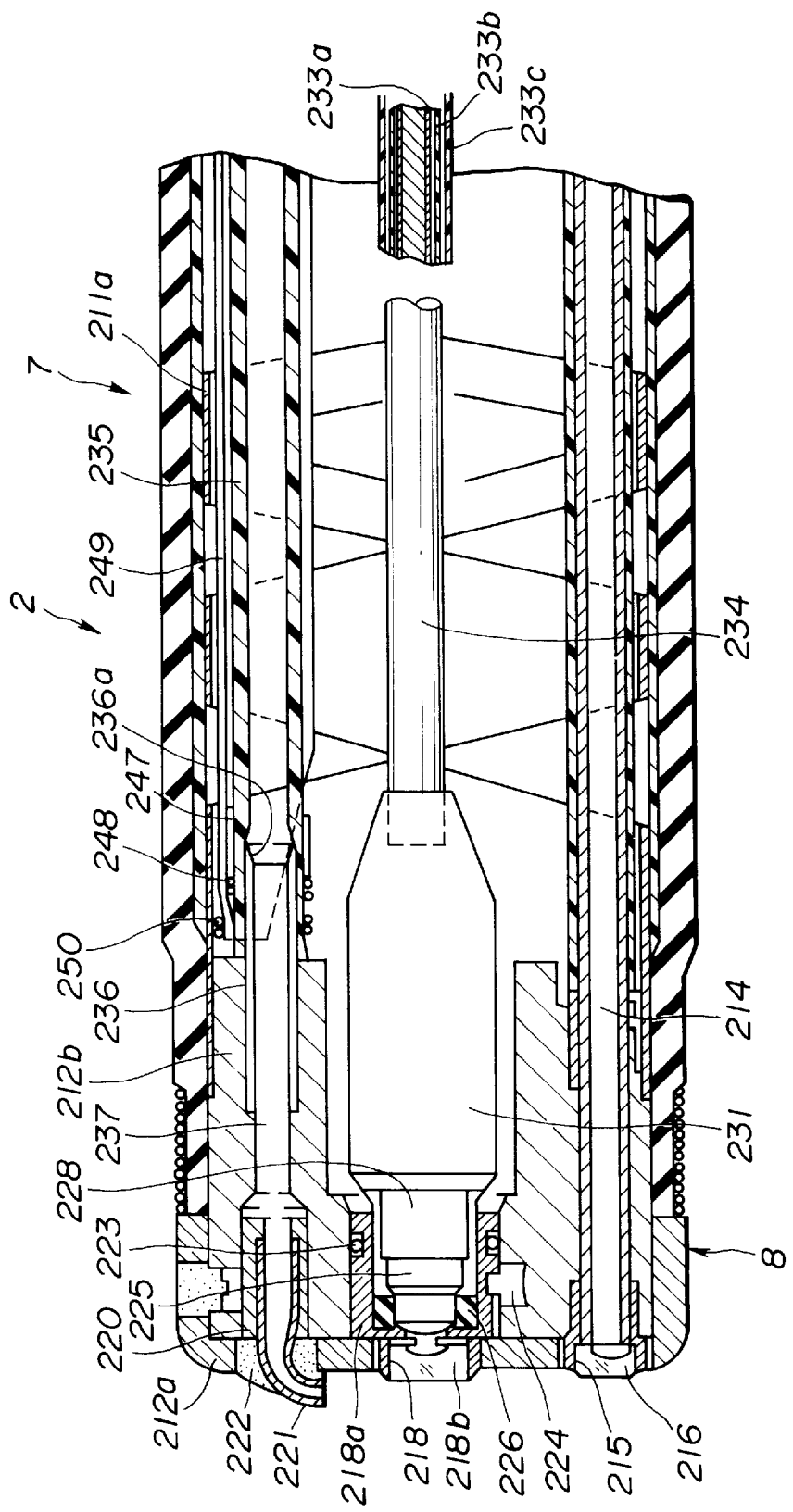
FIG. 32 is a cross-sectional view showing an arrangement of a forward end of an insertion of the endoscope.
Figure 33:
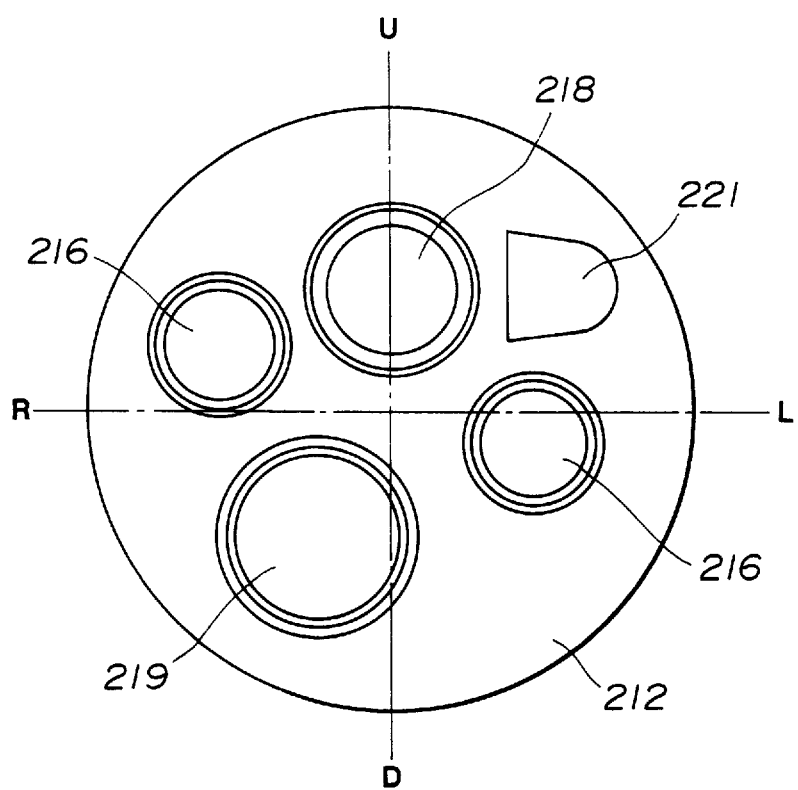
FIG. 33 is a top plan view showing the forward end of the insertion of the endoscope.

By the way, the forward-end hard quality 8 and the curvature 7 are arranged as shown in FIG. 32. As described previously, the illumination light from the light source device 5, which passes within the connection code 4 and through the interior of the endoscope 1 is so arranged as to be illuminated upon the part to be observed, through luminous intensity distribution lenses 216 which are fixed to a through hole 215 for illumination. FIG. 33 is a view in which the forward-end hard quality 8 is viewed from the front.

This forward-end hard quality 8 is formed with a through hole 218 for observation to which a cover lens 218b is interposed through a first lens frame 218a. The arrangement is such that observation of the part to be observed is performed through the through hole 218 for observation. Together therewith, the forward-end hard quality 8 is provided with the nozzle 221 for gas feeding and water feeding, which is oriented toward the cover lens 218b. The gas-feeding and water-feeding line changeover device 13 which is arranged on the operation 3 is operated whereby gas feeding and water feeding are performed to the cover lens 218b through the nozzle 221 so that a blur or the like on the surface of the cover lens 218b can be removed. The nozzle 221 is fixed to a forward-end cover 212a by, for example, adhesives 222 of a silicon system.

Furthermore, as shown in FIG. 33, the forward-end hard quality 8 is formed with a through bore or hole 219 for forceps. The through hole 219 for forceps is in communication with the forceps opening 10 which is formed in the operation 3, through a forceps channel (not shown) which is arranged within the insertion 2. The arrangement is such that the forceps which are inserted into the forceps opening 10 projects from the forward end of the insertion through the through hole 219 for forceps.

As shown in FIG. 33, the through hole 218 for observation is formed in a part which is opposed against the through hole 219 for forceps with a central axis of the forward-end hard quality 8 put therebetween.

The first lens frame 218a is fixed to the through hole 218 for observation by a fixing screw 224, and an O-ring 223 is interposed between the through hole 218 for observation and the first lens frame 218a so that a liquid tight state within the through hole 218 for observation is held by the O-ring 223.

Further, a second lens frame 225 is fixed on the side opposite to the cover lens 218b of the first lens frame 218a, through an insulation member 226. An objective lens system which comprises a plurality of lens groups which have an optical axis in accordance with an axial center of the through hole 218 for observation and an optical axis of the cover lens 218b is arranged within the second lens frame 225. Together therewith, an element frame 228 is covered on an outer periphery of the second lens frame 225 on the side opposite to the first lens frame 218a and is fixed. The element frame 228 extends rearwardly more than the second lens frame 225. To this extended part, a solid-state image pickup element (not shown) which forms an image pickup unit is fixed by adhesives of, for example, an epoxy system, perpendicularly to the optical axis of the objective lens system.

A shielding frame (not shown) which is covered by an insulation cover 231, which is cylindrically formed and which has an outer periphery thereof (formed by, for example, vinyl chloride or the like), has a forward end thereof which is fixed to the outer periphery of the element frame 228 on the side of proximal end thereof. A portion of the shielding frame on the side of the proximal end extends rearwardly. Within the extended part, a circuit substrate (not shown) which forms the image pickup unit, is held substantially in parallel with the optical axis. A lead line of the solid-state image pickup element is connected to the circuit substrate, and electric parts which form a drive circuit or a pre-amplifier, for example, ICs, transistors, capacitors or condensers and the like are fixed to the circuit substrate by solder or the like.

Figure 40:
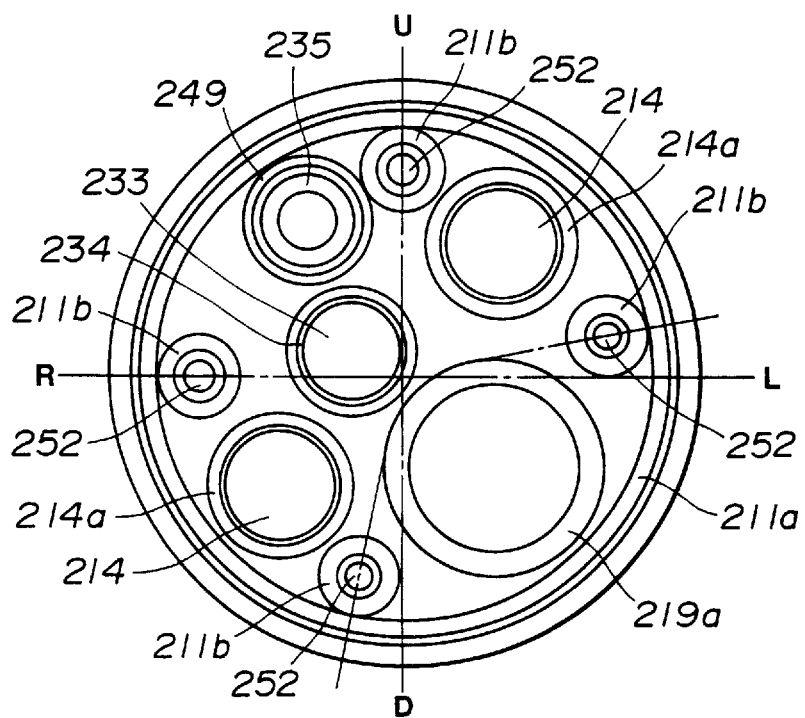
FIG. 40 is a cross-sectional view showing an internal arrangement of a curvature.

A signal cable 233 shown in FIG. 40, which consists of a plurality of unshown cables, is connected to the circuit substrate. A cable-protection tube 234 which is made of, for example, EPTFE or the like, is covered on an outer periphery of the signal cable 233. These are fixed to each other by adhesives of, for example, an epoxy system. The insulation cover 231 has a proximal end thereof the side of which extends up to an outer periphery of the adhesives, and the side of which is formed elongate more than the forward-end side of a cable protection tube 234. In this connection, it is preferable that a length of a portion at which the proximal-end side of the insulation cover 231 and the forward-end side of the cable protection tube 234 are overlapped with each other is equal to or more than 1.5 mm.

The signal cable 233 is formed as follows. A plurality of unshown cables, for example, are wound. An integrated shielding member 233a is covered on the signal cable 233. The signal cable 233 is fixed by a push and winding member 233b. Further, a cable skin 233c which is made of, for example, FEP or the like is covered on an outer periphery thereof. The signal cable 233 may be any one of a coaxial line and a single line in accordance with the use object.

Moreover, the endoscope, which is provided with a fluid line, is of the following structure. That is, a gas-feeding tube and a water-feeding tube which consist of, generally, an elastic tube are inserted and pass through the endoscope. These tubes join within the insertion or within the operation. At a convergence of the gas-feeding tube and the water-feeding tube, a three-forked branch pipe is provided. The two tubes are covered and fitted respectively over branch pipe parts of the branch pipe whereby the two tubes join together. The gas-feeding and water-feeding tube, which consists of an elastic tube has one end thereof that is connected to a junction pipe of the branch pipe. The other end thereof is connected to the gas-feeding and water-feeding tuber which is in communication with the gas-feeding and water-feeding tube at the forward-end forming part thereof.

The three-forked branch pipe is so arranged that a water-feeding pipe which is formed in curvature is joined substantially at a center of the linear gas-feeding pipe, by means of solder or the like. The following arrangement of the junction can be cited. That is, as disclosed in, for example, Japanese Utility Model Publication No. HEI 3-15048 (15048/1991) and Japanese Patent Unexamined Publication No. HEI 7-67831 (67831/1995), the junction has, on the side of the gas-feeding pipe, a connection hole whose inner diameter is smaller than an inner diameter of a junction of the water-feeding pipe, and the water-feeding pipe is joined to a periphery of the connection hole.

Furthermore, as the other arrangement example of the junction of the branch pipe, as disclosed in Japanese Patent Unexamined Publication No. HEI 7-79910 (79910/1995), there is an arrangement which is formed such that (a) curved pipe is abutted against an opening which is provided in a straight pipe and is joined thereto; (b) the opening is of size which is generally in conformance with an inner surface of the curved pipe; and (c) an inner wall at which the opening is formed is generally continuous with an interior of the curved pipe. The arrangement is such that the curved pipe is fixed with respect to the straight pipe by means of soldering or brazing and is joined thereto. When the soldering or brazing is performed, the braze is so arranged as to be performed under such a state that a wire which is inferior in adhesion of wax is inserted and passes through the interior of the curved pipe.

In a case of the former arrangement, since, in the branch pipe of the prior-art example, the diameter of the connection hole which is provided in the gas-feeding pipe is smaller than the inner diameter of the water-feeding pipe, a step is formed between the water-feeding pipe and an outer peripheral portion of the connection hole when the water-feeding pipe is connected to the gas-feeding pipe by soldering. For this reason, turbulent flow occurs at the step at the time of water feeding. Thus, a loss of an amount of water feeding was generated.

Further, due also to the fact that the gas-feeding and water-feeding tube is made short as far as possible in order to improve water break, there is a case where body liquid is drawn up to the interior of the three-forked branch pipe by capillary phenomena. Accordingly, it is necessary to perform cleaning of the interior of the fluid lines which include the branch pipe, after the use. However, the structure which has the step at the junction has had such a problem that the cleaning ability is not so much well.

Cleaning of the branch pipe is performed such that gas feeding and water feeding are repeated to thereby clean the same, normally, by tap water or running water or the like. However, in a case where filth or dirt or the like is mixed in mixture with the body liquid, the filth or the like is apt to be stayed on the step. Thus, there was a case where cleaning is not sufficiently performed, and time is taken or time is consumed for the cleaning. Furthermore, there is a case where an extremely thin brush or the like is inserted and passes through the interior of the line to perform the cleaning. However, also in this case, hairs of the brush do not sufficiently impinge against the step so that the cleaning cannot easily be performed.

Further, in a case of the latter arrangement, the arrangement is such that the wall surface of the opening in the straight pipe and the inner surface of the curved pipe are joined to each other continuously. However, it is extremely difficult to work the opening so that the inner walls are continuous to each other. Moreover, it is an extremely difficult technique to align a position of the wall surface of the opening in the straight pipe and a position of the inner surface of the curved pipe to each other. Workability is inferior, and variation becomes large or high. Thus, the positions are apt to be shifted from each other. In a case where the shifting occurs in the junction, a step is generated at a portion between the opening and the curved pipe. There is generated such a problem that, similarly to the case of the former arrangement, filth is apt to be stayed or collected so that the cleaning ability is deteriorated. Furthermore, since the shape of the opening is determined in a single direction by the shape of the curved pipe, there was a fear that the straight pipe is connected thereto in a reverse or counter direction.

In view of the above, an arrangement example of the fluid line will be shown below, which has a gas-feeding and water-feeding line junction which can join, with superior workability and extremely smoothly, an inner periphery of, particularly, the junction of the three-forked branch pipe, in which a loss of an amount of water feeding is less or low, and which is superior in cleaning ability.

A gas-feeding and water-feeding tube 235 extends within the insertion 2. The gas-feeding and water-feeding tube 235 has a forward end thereof the side of which is connected to a connection pipe 236 by, for example, adhesives of an epoxy system. The connection pipe 236 is connected to a forward end body 212b. The connection pipe 236 is in communication with the nozzle 221 which is provided on the side of the forward end, through a gas-feeding and water-feeding line 237 of the forward end body 212b. The nozzle 221 is fixed to a nozzle mounting tube 220 which is fixed to the interior of the forward end body 212b, by, for example, adhesives of an epoxy system, or the like. The side of the forward end thereof is exposed from a forward-end cover 212a.

Figure 34:
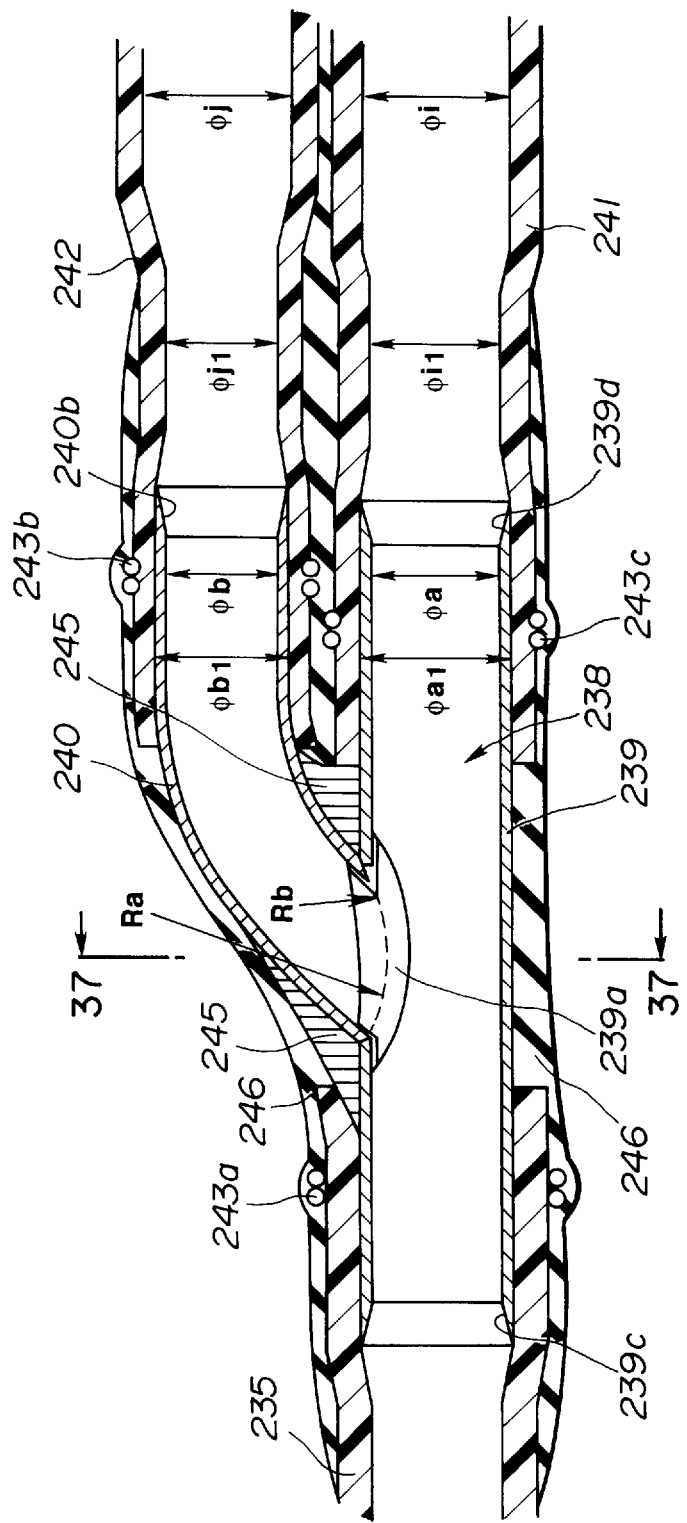
FIG. 34 is a cross-sectional view showing an arrangement of a three-forked branch pipe which Joins the gas-feeding line and the water-feeding line to each other.

As shown in FIG. 34, the proximal-end side of the gas-feeding and water-feeding tube 235 is fixed or secured to the forward-end side of a converging pipe 239 of a three-forked branch pipe 238 which comprises a converging pipe 239 and a branch pipe 240 which are provided within the insertion 2, by means of, for example, adhesives of an epoxy system or the like. A gas-feeding tube 241 and a water-feeding tube 242 are fixed to the proximal-end side of the converging pipe 239 of the three-forked branch pipe 238 and the proximal-end side of the branch pipe 240, similarly, by means of, for example, adhesives of an epoxy system, or the like.

A connection between the tube and the three-forked branch pipe 238 may be secured more firmly such that outer peripheries thereof are tied up by, for example, threads 243a, 243b and 243c, and adhesives of an epoxy system, for example, are applied to the outsides of these threads 243a, 243b and 243c. As the threads 243a, 243b and 243c, a silk thread or yarn, a fishing gut or the like is used, for example.

As the gas-feeding and water-feeding tube 235, the gas-feeding tube 241 and the water-feeding tube 242, a tube is suitable or appropriate, which is made of, for example, PTFE or the like which has elasticity. Alternatively, polyethylene (such as, Illux or the like), or a tube for medial treatment (such as, EVA or the like) may be used.

A connection hole 239a for being connected to the branch pipe 240 is provided substantially at a center of the converging pipe 239. If a cross-section of the connection hole 239a is taken, the cross-section becomes a uniform radius Ra. On one hand, a surface of the branch pipe 240 which is abutted against the connection hole 239a is made to a uniform radius Rb, similarly to the cross-section of the connection hole 239a. Here, it is desirable that the relationship between Ra and Rb is Ra=Rb. However, although slightly different from each other by working variation, it is preferable that an absolute value |Ra−Rb| of a difference therebetween remains within 10% of an inner diameter φa of the converging pipe 239 or an inner diameter φb of the branch pipe 240.

Figure 35:
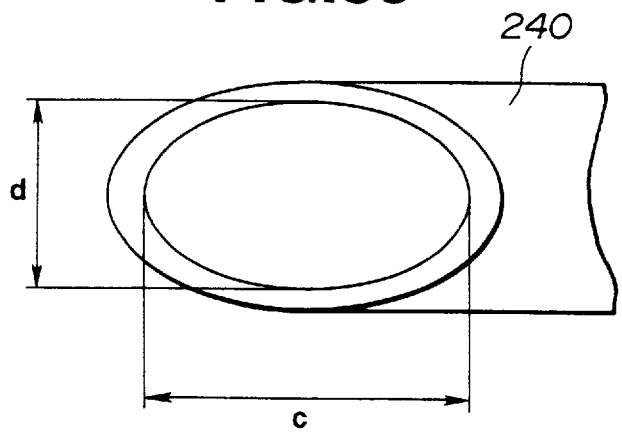
FIG. 35 is an arrangement explanatory view showing an abutment surface of the branch pipe which forms the three-forked branch pipe.

The abutment surface of the branch pipe 240 is an ellipse in shape, as shown in FIG. 35, if seen from the side of the connection hole 239a. Here, it is assumed that a length of an inner periphery of the abutment surface in a direction of a major axis is c, and a length in a direction of a minor axis is d.

Figure 36:
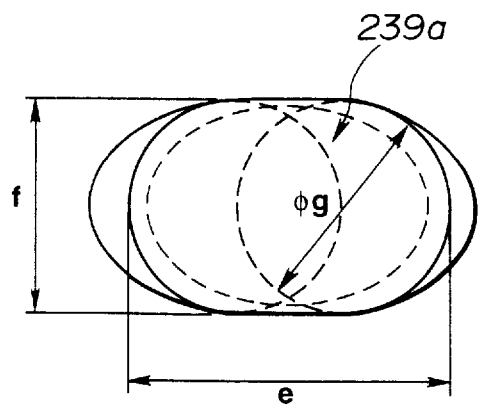
FIG. 36 is an arrangement explanatory view showing a connection hole in a converging pipe which forms the three-forked branch pipe.

On one hand, the connection hole 239a in the converging pipe 239 is such that, if an elliptic hole is so bored that the cross-section has the uniform radius Ra as described above, an end surface thereof is made to a hole which comprises an elliptic form at the outermost periphery and an inside elliptic form shown by a broken line, as shown in FIG. 36, as viewed from the side of the branch pipe 240. If the hole remains to the elliptic form shown by the broken line, the hole remains smaller or low less than the inner periphery of the abutment surface of the branch pipe 240. Accordingly, the hole is further shaved in the form of an edge, and is made to a hole as shown by the solid line. At this time, as shown in FIG. 36, the connection hole 239a is so worked as be made to d≦g and c≦e, by a cutter, an end mill or the like which has an outer diameter φg. Alternatively, working may be performed by a laser cutter or the like. Here, it is assumed that a length of an inner periphery of the connection hole 239a in the major-axis direction is e, while a length in a minor-axis direction is f. In this connection, it is desirable that working is performed while the shape of the radius Ra in the cross-section remains.

Moreover, an outer periphery of the connection hole 239a is so worked as to become larger than an inner periphery of the abutment surface of the branch pipe 240 over the entire range or region. Furthermore, it is desirable that an outer periphery of the abutment surface of the branch pipe 240 is smaller than an outer periphery of the connection hole 239a. The converging pipe 239 becomes the form symmetric to the left and the right around a center of the connection hole 239a.

Figure 37:
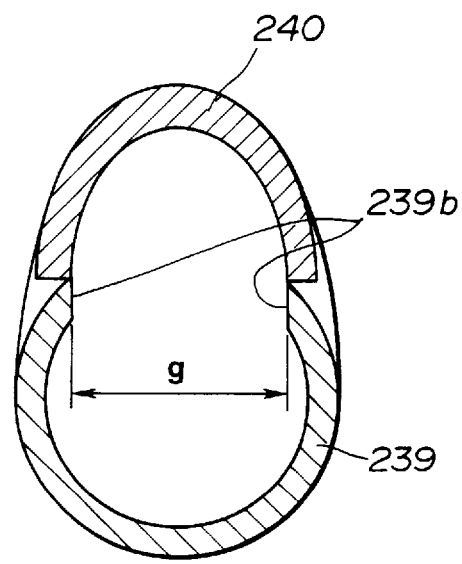
FIG. 37 is a cross-sectional view of a connection between the converging pipe and the branch pipe.

FIG. 37 shows a cross-section taken along a line 37—37 in FIG. 34. Here, if an inner diameter of the converging pipe 239 is φa, while an inner diameter of the branch pipe 240 is φb, it is desirable that the relationship of size or dimension among parts is made to b=d≦g≦a because cutting work of a diameter φg is performed to the connection hole 239a in the converging pipe 239.

Wall surfaces 239b of the converging pipe 239, which are to be worked in shaving, are smoothly connected to an inner surface of the branch line 240. Further, the wall surfaces 239b are also used as a guide surface for a core 244 to be described later, which is used at the time of assembling. The wall surface 239b exists on the connection hole 239a over the whole periphery thereof.

The converging pipe 239 and the branch pipe 240 are connected to each other in this manner, whereby the three-forked branch pipe 238 is assembled.

Here, an assembling method of the three-forked branch pipe 238 will be described in detail. When the converging pipe 239 and the branch pipe 240 are connected to each other, the branch pipe 240 is abutted against the connection hole 239a in the converging pipe 239 so that both are fixedly secured to each other. This fixed securing is performed by a solder 245 which is shown, for example, in FIG. 34.

Figure 38:
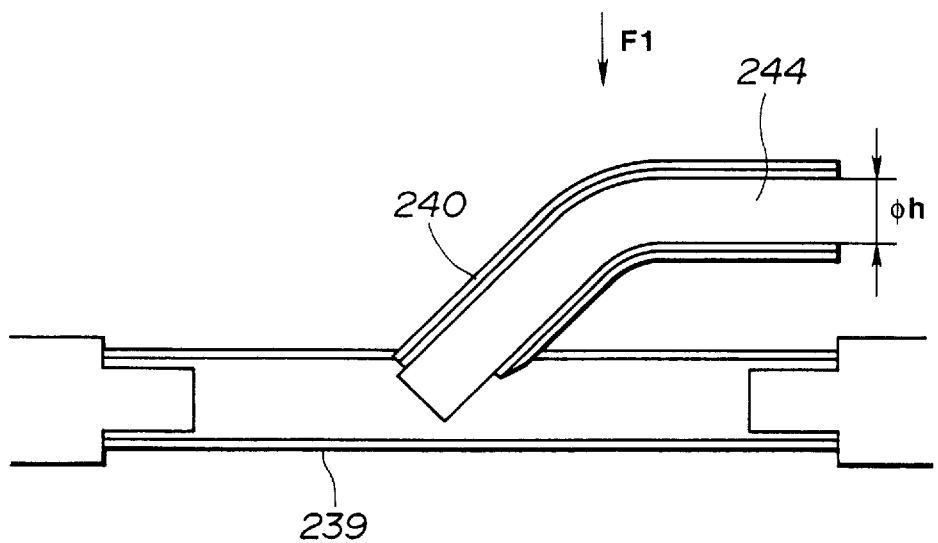
FIG. 38 is an explanatory view showing a positioning state at the time the converging pipe and the branch pipe are connected to each other.

At the time of soldering, as shown in FIG. 38, the core 244 which is used both as functions of prevention of invasion to the converging pipe 239 and the inner surface of the branch pipe 240, positioning thereof and degasing thereof is inserted into the side of the abutment surface from the side of the proximal end of the branch pipe 240. The core 244 is formed by synthetic resin which is higher in melting point than the solder, is inferior in heat conductivity. The solder is difficult to adhere, and has elasticity, for example, PTFE (polytetrafluoroethylene) or the like. The forward-end side of the core 244 is inserted until such order as to be caught in the converging pipe 239. Here, if it is assumed that the outer diameter of the core is φh, it is desirable that φh is made to the order of φh=φb×0.9~0.98. In this connection, in the present arrangement example, the core is inserted only into the branch pipe 240. However, another core may be inserted into the converging pipe.

When the core 244 is abutted against the converging pipe 239 under a condition inserted into the branch pipe 240, the wall surfaces 239b which are provided on the connection hole 239a guide the core 244 so that positioning of the branch pipe 240 and the converging pipe 239 in the left and right directions can be performed. Moreover, if the core 244 is pressed or urged against the converging pipe 239 by a capacity of F1, for example, 300 gf~600 gf from an upper part of the branch pipe 240, by means of jig or the like, the radius Ra of the connection hole 239a intends to be coincident with the radius Rb of the abutment surface of the branch pipe 240. Accordingly, it is possible to conform the positions in the forward and rearward directions to each other. Furthermore, since the converging pipe 239 is in the form symmetrical to the left and the right around the connection hole 239a, it is unnecessary at all to mind or care of the directions when the branch pipe 240 is connected.

Moreover, at the time of soldering, it is necessary to perform degasing when a flux which is applied previously is evaporated. Since, when the converging pipe 239 and the branch pipe 240 are in intimate contact with each other, there is the possibility that cavities or blow holes are formed, a gap t is defined in the converging pipe 239 and the branch pipe 240 in order to cause the solder to completely flow around the whole periphery of the connection surface. The gap t should be set within a range between 0.02~0.1 mm. This gap t may be set mechanically by a jig or the like. Alternatively, this gap t may be such that the converging pipe 239 and the branch pipe 240 are set under a state in which a gap t1 is previously defined, and the converging pipe 239 and the branch pipe 240 are pressed against each other by capacity of F1 to perform positioning and, then, the converging pipe 239 and the branch pipe 240 are returned to the gap t by the elastic force of the branch pipe 240. Here, it is desirable that t1=t×1.1~1.5.

If soldering is performed under a state in which the gap is defined therebetween in this manner, since the core 244 exists around the entire periphery of the connection surface, the gas in which the flux which is previously applied is evaporated, or the gas which is generated from the solder does not enter the converging pipe 239 and the branch pipe 240, but escapes to the outside by the gap t. Further, the gas which enters the inside is so arranged as to escape from the forward-end side or the proximal-end side of the converging pipe 239.

Moreover, since the solder 245 is difficult to adhere to the core 244, and the outer diameter $\phi h$ thereof is approximate to the inner diameter $\phi b$ of the branch pipe 240, and the heat conductivity or thermal conductivity thereof is also low, the solder is difficult to flow into the inner surfaces of the converging pipe 239 and the branch pipe 240. Accordingly, the solder 245 is filled up to the thickness of the gap t of the surface where the converging pipe 239 and the branch pipe 240 are abutted against each other. In this connection, even if the solder 245 enters the inside of the converging pipe 239 and the branch pipe 240 from the gap, since the heat conductivity of the core 244 is low, and the solder 245 is difficult to adhere thereto, the solder 245 flows into the inner surfaces of the converging pipe 239 and the branch pipe 240 in a very thin manner. Accordingly, no step occurs.

In this manner, since the solder 245 flows into the connection between the converging pipe 239 and the branch pipe 240, and the inner surface configuration or shape can be positioned by the core 244 and is formed, it is possible to tie the converging pipe 239 and the branch pipe 240 to each other by the solder under a state in which the inner surface of the connection is kept smooth. Here, even if the position of the branch pipe 240 is shifted slightly, no step occurs because the inner surface of the abutted surface is smaller than the connection hole 239a. Thus, it is possible to connect the converging pipe 239 and the branch pipe 240 to each other surely and smoothly.

On one hand, on the outer periphery of the junction between the converging pipe 239 and the branch pipe 240, the solder 245 is piled up in order to increase the joining strength so that soldering is performed more firmly. At this time, it is desirable that temperature of a trowel forward-end of a trowel which performs the soldering is 215° C.±5° C. Furthermore, the arrangement may be such that the solder is piled up on the outer periphery of the junction and, thereafter, the outer periphery is shaved by a file or the like. Thus, the converging pipe 239 and the branch pipe 240 are smoothly be tied to each other.

By the way, the gas feed tube 241 and the water feed tube 242 have respective inner diameters thereof which, as shown in FIG. 34, are larger than outer diameters $\phi a1$ and $\phi b1$ of the respective converging pipe 239 and branch pipe 240, and are made respectively to $\phi i$ and $\phi j$. Here, when the gas-feeding tube 241 and the water-feeding tube 242 are secured respectively to the converging pipe 239 and the branch pipe 240, thermal forming, for example, or the like is performed to the gas-feeding tube 241 and the water-feeding tube 242 such that the relationship $\phi i1<\phi a1<\phi i$, $\phi j1<\phi b1<\phi j$ is obtained, the diameters thereof are reduced to $\phi i1$ and $\phi j1$, and then, the gas-feeding tube 241 and the water-feeding tube 242 are secured respectively to the converging pipe 239 and the branch pipe 240 after the inner diameter has been reduced to $\phi i1$ and $\phi j1$.

In this manner, the tube is connected whereby the gas-feeding tube 241 and the water-feeding tube 242 are made further difficult to escape. Thus, it is possible to secure a large amount in the amount of gas feeding and the amount of water feeding. Further, the tube is thermally formed whereby the wall thickness of the tube at a portion to be fitted is made thin. Thus, it is possible to reduce the outer diameter of the portion of the three-forked branch pipe 238. Moreover, in the present example, the whole outer periphery of the three-forked branch pipe 238 is covered with, for example, adhesives 246 of an epoxy system, whereby the aforesaid portion, which is thinned in wall thickness, is reinforced, and it is prevented that catching with respect to other visceral objects occurs, and motion is deteriorated.

On one hand, the converging pipe 239 and the branch pipe 240 are secured respectively to the tubes (the gas-feeding and water-feeding tube 235, the gas feed tube 241 and the water-feeding tube 242). However, since steps corresponding respectively to the wall thicknesses of the pipes occur on the inside of the tube connection, the converging pipe 239 and the branch pipe 240 are provided, at ends thereof, with tapered surfaces 239c, 239d and 240b. Thus, the arrangement is such that steps do not occur to the utmost.

In the three-forked branch pipe 238 which is assembled in this manner, the wall surface of the connection between the converging pipe 239 and the branch pipe 240 and the connections with respect to the respective tubes are made to form which has no irregularities substantially completely. Thus, when cleaning water and fluid for cleaning such as pressurized air or the like are ventilated, there is no portion where a diameter thereof is abruptly reduced. Accordingly, no turbulent flow is generated, and it is possible to cause the fluid having a large flow rate to flow smoothly without loss. Thus, it is possible to effectively perform cleaning or the like of the observation window.

Moreover, since there is no step in the connection between the converging pipe 239 and the branch pipe 240, or the like, cleaning ability is superior. It is possible to smoothly and surely perform the cleaning when the cleaning which is performed every the use is performed. No dirt is adhered to a part thereof.

Furthermore, in the present arrangement, positioning between the converging pipe 239 and the branch pipe 240 is easy, and it is possible to surely perform soldering around the entire periphery to connect them to each other without the fact that cavities are formed in the solder. Further, because of the connection due to the soldering, it is possible to perform assembling of the three-forked branch pipe 238 at a low cost and simply.

By the way, the forward-end hard quality 8 of the endoscope 1 is provided, as shown in FIG. 33, with a cover lens 218b at a center slightly upwardly as viewed from the forward end, the through-hole 219 for forceps in a leftward and downward direction of the center, the luminous intensity distribution lens 216 substantially horizontally in a left direction of the cover lens 218b, the another luminous intensity distribution lens 216 in a right downward direction, and the nozzle 221 substantially horizontally in a right direction. In this connection, in subsequent FIG. 33 and FIGS. 39 to 42, U, D, R and L correspond respectively to curved directions to upper, lower, left and right directions of the curvature.

Since the two luminous intensity distribution lenses 216 are located respectively at substantially symmetric positions, with respect to a straight line which joins the center of the through hole 219 for forceps and the center of the cover lens 218b to each other, this arrangement is efficient also in view of luminous intensity distribution. Further, the nozzle 221 is arranged at a position close to the cover lens 218b. Accordingly, response of the gas feeding and the water feeding is superior, and the water break is made superior. Particularly, this is an arrangement which is effective for an endoscope for a lower digestive organ.

As shown in FIG. 32, the connection pipe 236 which is in communication with the nozzle 221 has a tapering surface 236a on the side of one end thereof which is connected to the gas-feeding and water-feeding tube 235. Thus, a step with respect to the inner surface of the gas-feeding and water-feeding tube 235 is eliminated to the utmost. Moreover, in order to prevent the gas-feeding and water-feeding tube 235 from being swung at the end of the connection pipe 236, and the adhesives being broken away or separated, the end of the gas-feeding and water-feeding tube 235 is covered with a thermal-contraction tube 247. The gas-feeding and water-feeding tube 235 has an end thereof which is firmly fastened or tightened on the connection pipe 236 which is not covered with the heat-contraction tube 247, by threads 248, and which is secured by adhesives of an epoxy system.

Furthermore, the gas-feeding and water-feeding tube 235 is covered with a protection tube 249 which is formed by, for example, EPTFE or the like, over substantially the entire length thereof from the forward end to the three-forked branch pipe 238 on the side of the proximal end. The protection tube 249 is fixed after the gas-feeding and water-feeding tube 235 has previously been inserted into the interior thereof, and the gas-feeding and water-feeding tube 235 has been secured to the connection pipe 236.

Since the protection tube 249 has an inner diameter thereof which is smaller than an outer diameter of a portion which is covered with the heat-contraction tube 247, a portion thereof is cut obliquely or diagonally from a position about half the forward end of the protection tube 249 to a position whose length is 1.2~1.5 times the heat-contraction tube 247 on the side of the proximal end thereof. Under this state, the protection tube 249 is assembled, whereby it is possible to cover the forward end of the protection tube 249, exceeding the heat-contraction tube 247 to the connection pipe 236. In the present example, as shown in FIG. 32, the forward end of the protection tube 249 and the forward end of the gas-feeding and water-feeding tube 235 are caused to be generally coincident with each other and are fixed or secured to each other. The forward end of the protection tube 249 and the forward end of the gas-feeding and water-feeding tube 235 are fastened to each other by threads 250 thereon and are secured to each other more firmly by the adhesives of the epoxy system or the like thereon.

Figure 39:
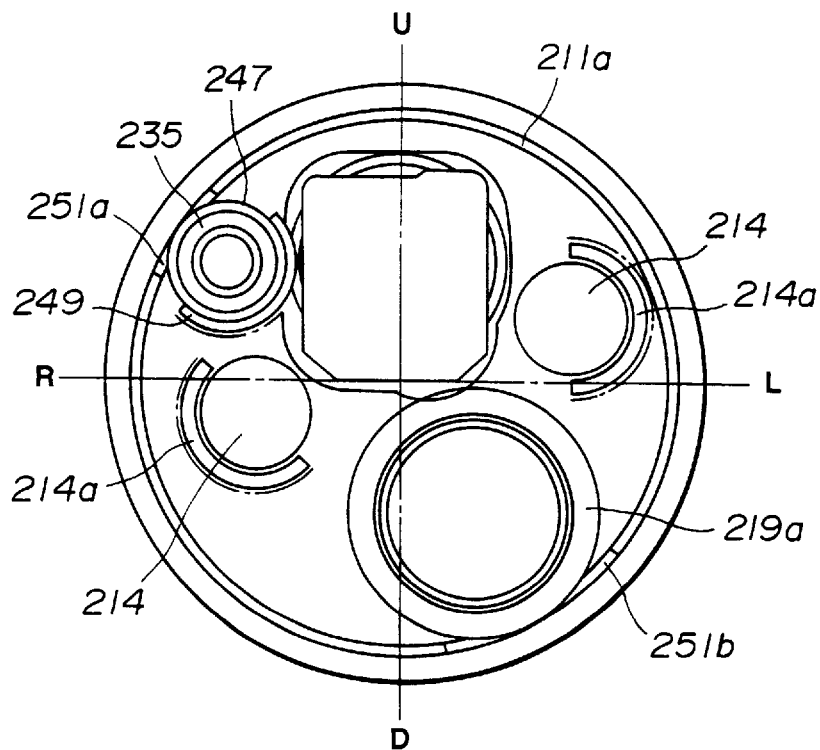
FIG. 39 is a cross-sectional view showing an internal arrangement of a connection with respect to a first curvature piece or frame on the side of a rearward end of a forward end.

FIG. 39 shows a line 39—39 cross-section in FIG. 32. The direction in which the aforesaid protection tube 249 is cut is oriented toward the outward of a first curved frame 211a in the radial direction. This first curved frame 211a is provided with cuts 251a and 251b in portions of the forceps channel 219a which is connected to the gas-feeding and water-feeding tube 235 and the through hole 219 for forceps. A part of the visceral object is caused to fly out into the cuts 251a and 251b whereby it is possible to reduce a diameter of the forward-end hard quality 8.

In the present example, the part of the forceps channel 219a is caused to fly out from an inner surface only for substantially the wall thickness of the first curved frame 211a, and the part of the gas-feeding and water-feeding tube 235 is similarly caused to fly out from the inner surface only for substantially the wall thickness of the first curved frame 211a. In this connection, here, the cut side of the protection tube 249 is caused to fly out into the cut 251a, whereby an attempt can further be made to reduce the diameter of the forward-end hard quality 8. Moreover, light guides 214 may also be covered similarly with a light-guide protection tube 214a so that ends thereof are cut obliquely, similarly to the protection tube 249.

An internal arrangement of the curvature 7 on the side of the rearward end of the forward-end hard quality 8 is shown in FIG. 40. Arranged within the curvature 7 are a curvature wire 252 which performs traction by curvature operation of the curvature operation knob of the operation 3, and a wire guide 211b which guides this curvature wire 252, together with the signal cable 233, the forceps channel 219a, two light guides 214, a gas-feeding and water-feeding tube 235. The wire guide 211b is provided within the curvature frame 211a, meeting curvature in four, upper, lower or down, left and right (U, D, R and L) directions. The curvature wires 252 are inserted into and pass through the respective wire guides 211b.

In connection with the above, as shown in FIG. 40, the wire guides 211b may be arranged such that, in order to avoid interference with respect to the visceral object, the wire guide on the right side (R) as viewed, for example, from the side of hand is swung to the up-side (U), and the wire guide on the down side (D) is swung to the left side (L).

The aforesaid two light guides 214 are low in flexibility as compared to the signal cable 233, the forceps channel 219a and the gas-feeding and water-feeding tube 235. Further, since the signal cable 233 performs supply of a drive signal to an unshown solid-state image pickup element which is provided at the forward end thereof and a power source, it is preferable or desirable in view of tolerance or resistance to minimize motion of the signal cable 233 in the curvature operation. Accordingly, in the present example, the arrangement is such that the signal cable 233 is arranged substantially at a center of the curvature frame 211a, the forceps channel 219a is arranged at a right lower part, the gas-feeding and water-feeding tube 235 is arranged at a left upper part, and the two light guides 214 are arranged respectively at a right upper part and a left lower part.

With such structural arrangement, since the gas-feeding and water-feeding tube 235, the signal cable 233 and the forceps channel 219a, which are high in elasticity, stand substantially in a line, curvature can be applied thereto by substantially equal capacity even in curvature in any directions; such as, curvature of a twist shape or the like, including an up-direction, a down-direction, a right-direction and a left-direction. Furthermore, the signal cable 233 is located substantially at a center, and other visceral objects are substantially equally arranged around the same. Accordingly, it is possible to prevent the arrangement or configuration of the visceral objects from being disturbed. Thus, it is possible to improve the tolerance or resistance of the signal cable 233 and the light guides 214 due to the curvature operation.

Figure 41:
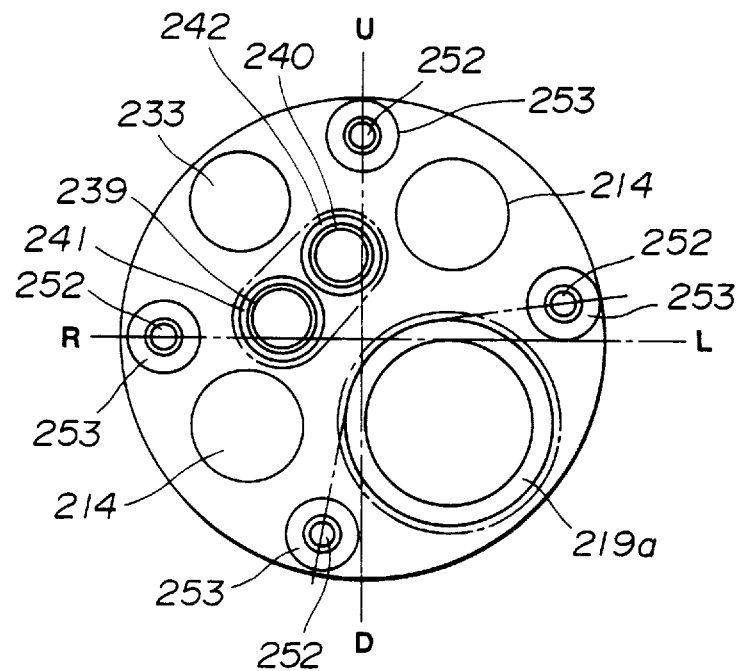
FIG. 41 is a cross-sectional view showing an internal arrangement of a three-forked branch pipe portion in an elastic pipe of the insertion.
Figure 42:
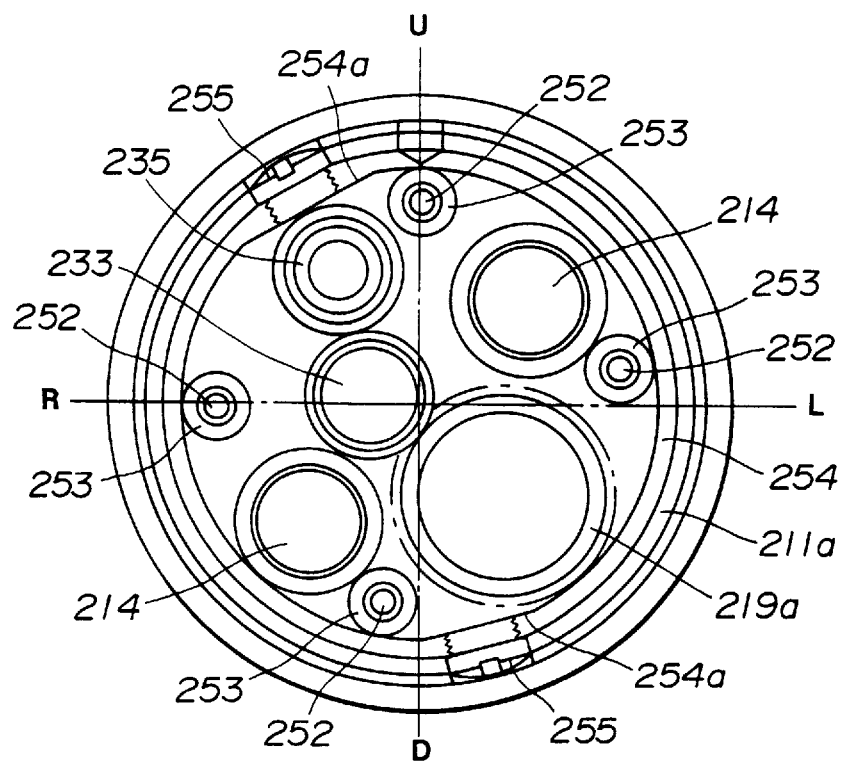
FIG. 42 is a cross-sectional view showing an internal arrangement of a connection portion between a forward-side base of the elastic pipe of the insertion and the curvature frame at the rearward end thereof.

An internal arrangement in a flexible pipe of the insertion 2 on the side of the rearward end of the curvature 7 is shown in FIGS. 41 and 42. FIG. 41 is a cross-sectional view of an arrangement of the three-forked branch pipe 238, while FIG. 42 is a cross-sectional view of a portion of a forward-side base 254 which is connected to the curvature 7. The curvature frame 211a at the rearward end of the curvature 7 is connected to and is fixed to the forward-side base 254, whereby the curvature 7 is connected to the flexible pipe.

The arrangement is such that, within the flexible pipe of the insertion 2, the signal cable 233 and the gas-feeding and water-feeding tube 235 are crossed, on the way, each other in or around the clockwise direction, and the signal cable 233 is arranged on the outside of the insertion 2 in the radial direction, whereby the arrangement disturbance of the visceral objects is prevented more firmly. The gas-feeding and water-feeding tube 235 has a proximal end thereof which is connected to the three-forked branch pipe 238, and which is connected to the gas-feeding tube 241 and the water-feeding tube 242 through the converging pipe 239 and the branch pipe 240. Furthermore, the aforementioned curvature wire 252 has a rearward end thereof the side of which is inserted into and passes through a corresponding guide coil 253 which is secured only to a forward-side base 254 of the insertion 2, and the side of which is guided to the operation 3 by the guide coil 253.

A forward-side base 254 of the insertion 2 and the curvature frame 211a at the rearward end are secured to each other by two screws 255 which are provided generally opposite to each other. In this fixture, a wall thickness of the forward-side base 254 is necessary for a length of the thread of the screws 255. In the present example, however, the arrangement is such that a horizontal surface part 254a, which is thicker in thickness than the other portions, is provided whereby the wall thickness is secured, and the threads of the screws 255 do not fly out to the inner surface.

It is desirable that the aforementioned horizontal surface 254a is provided on a portion which does not relatively affect an influence upon the visceral objects. Reversely, however, the aforementioned horizontal surface 254a may be provided on a portion which restrains or suppresses the visceral objects (regulates motion). Further, the arrangement may be such that the forward-side base 254 and the curvature frame 211a are secured to each other by, for example, adhesives of an epoxy system and, then, are fixed to each other by the screws 255.

With such arrangement, the outer diameter of the forward-side base 254 can be reduced by a degree in which the horizontal surface 254a is provided inside to secure the wall thickness of the thread of the screw 255 and, accordingly, it is possible to reduce the diameter of the insertion 2.

In this invention, it is apparent that working modes different in a wide range can be formed on the basis of this invention without departing from the spirit and scope of the invention. This invention is not restricted by any specific embodiments except being limited by the appended claims.

What is claimed is:

1. A line changeover device for an endoscope, comprising a cylinder, and a piston which is fitted and inserted into the cylinder in a retractable manner, for changing over a line which is arranged in the endoscope, wherein a seal member which is abutted against said cylinder to retain at least one of water tightness and gas tightness with respect to the cylinder is fixedly provided on an outer periphery of said piston, and a strength reinforcement is provided on at least a part between an outer periphery of said seal member and an inner periphery thereof, wherein said seal member has a deformable portion which deforms, when said piston is fitted into said cylinder, at an end portion of said strength reinforcement located on said outer periphery of said seal member.

2. A line changeover device for an endoscope, according to claim 1, wherein material of said strength reinforcement and material of said seal are formed respectively by materials different from each other.

3. A line changeover device for an endoscope, according to claim 1, wherein said strength reinforcement is provided at least at one surface of an upper surface of said seal member and a lower surface thereof.

4. A line changeover device for an endoscope, comprising a cylinder, and a piston which is fitted and inserted into the cylinder in a retractable manner, for changing over a line which is arranged in the endoscope, wherein a seal member which is abutted against said cylinder to retain at least one of water tightness and gas tightness with respect to the cylinder is fixedly provided on an outer periphery of said piston, strength reinforcements, having at least a deformable portion, are provided between an outer periphery of said seal member and an inner periphery thereof, and said strength reinforcements are provided respectively on both upper and lower surfaces of said piston in a sliding direction.

5. A line changeover device for an endoscope, according to any one of claims 1–4.

wherein material of said seal member is natural rubber.

6. A line changeover device for an endoscope, according to any one of claims 1–4, wherein material of said seal member is synthetic rubber.

7. A line changeover device for an endoscope, according to claim 6, wherein silicon rubber is used as the material of the synthetic rubber which forms said seal member.

8. A line changeover device for an endoscope, according to claim 6, wherein the synthetic rubber which forms said seal member has hardness which is no more than 55°.

9. A line changeover device for an endoscope, according to any one of claims 1–4, wherein material of said seal member is synthetic resin.

10. A line changeover device for an endoscope, according to any one of claims 1–4, wherein material of said seal member is elastomers.

11. A line changeover device for an endoscope, according to claim 1 or 4, wherein a plurality of said strength reinforcements are provided between an outer periphery and an inner periphery of said seal member.

12. A line changeover device for an endoscope, according to claim 1 or 4, wherein said strength reinforcement is provided at a portion other than said deformable portion, said deformable portion being deformed when said seal member is fitted and inserted into the interior of said cylinder.

13. A line changeover device for an endoscope, according to claim 1 or 4, wherein said strength reinforcement is provided around the whole periphery between an outer periphery of said seal member and an inner periphery thereof.

14. A line changeover device for an endoscope, according to claim 1 or 4, wherein said strength reinforcements are provided respectively at portions other than at least adjoining regions, of portions in which an outer periphery of said seal member is divided into equal spaces.

15. A line changeover device for an endoscope, according to claim 4, wherein said strength reinforcements are provided respectively at positions which are asymmetric to each other in an upper surface of said seal member and a lower surface thereof.

16. A line changeover device for an endoscope, according to claim 5, wherein said strength reinforcements have respective magnitudes thereof which are different in an upper surface of said seal member and a lower surface thereof.

17. A line changeover device for an endoscope, according to claim 16, wherein the strengths of said strength reinforcements which are provided on an upper side of said seal member are larger than the strengths of said strength reinforcements which are provided on a lower side of said seal member.

18. A line changeover device for an endoscope, according to claim 16, wherein the strengths of said strength reinforcements which are provided on a lower side of said seal member are larger than the strength of said strength reinforcements which are provided on an upper side of said seal member.

* * * * *